United States Patent
Schoepgens et al.

(10) Patent No.: US 10,179,099 B2
(45) Date of Patent: Jan. 15, 2019

(54) DECOLORIZATION OF DYED KERATIN FIBERS

(71) Applicant: Henkel AG & Co. KGaA, Duesseldorf (DE)

(72) Inventors: Juergen Schoepgens, Schwalmtal (DE); Burkhard Mueller, Duesseldorf (DE)

(73) Assignee: Henkel AG & Co. KGaA, Desseldorf (DE)

( * ) Notice: Subject to any disclaimer, the term of this patent is extended or adjusted under 35 U.S.C. 154(b) by 0 days.

(21) Appl. No.: 15/535,302

(22) PCT Filed: Nov. 5, 2015

(86) PCT No.: PCT/EP2015/075785
§ 371 (c)(1),
(2) Date: Jun. 12, 2017

(87) PCT Pub. No.: WO2016/091492
PCT Pub. Date: Jun. 16, 2016

(65) Prior Publication Data
US 2017/0326055 A1 Nov. 16, 2017

(30) Foreign Application Priority Data

Dec. 11, 2014 (DE) ........................ 10 2014 225 545

(51) Int. Cl.
*A61Q 5/08* (2006.01)
*A61K 8/46* (2006.01)
*A61K 8/41* (2006.01)
*A61Q 5/10* (2006.01)

(52) U.S. Cl.
CPC ................ *A61K 8/466* (2013.01); *A61K 8/41* (2013.01); *A61K 8/46* (2013.01); *A61Q 5/08* (2013.01); *A61Q 5/10* (2013.01); *A61K 2800/262* (2013.01)

(58) Field of Classification Search
CPC ............. A61Q 5/10; A61K 8/466; A61K 8/46
See application file for complete search history.

(56) References Cited

U.S. PATENT DOCUMENTS 6,730,132 B1 * 5/2004 Beckmann ............ C07C 309/08
8/137

FOREIGN PATENT DOCUMENTS

| DE | 102006053343 A1 | 8/2007 |
|----|-----------------|--------|
| DE | 102006022274 A1 | 11/2007 |
| DE | 102006053402 A1 | 5/2008 |
| EP | 1300136 A2 | 4/2003 |
| WO | 2007107310 A2 | 9/2007 |
| WO | 2008055756 A1 | 5/2008 |

OTHER PUBLICATIONS

STIC Search Report dated Sep. 7, 2017.*
EPO, International Search Report and Written Opinion issued in International Application No. PCT/EP2015/075785, dated Dec. 21, 2015.
BASF, "Cyclanon ECO", Colorants and Finishing Products, Jan. 2000, [online]. [Retrieved on Nov. 27, 2015]. Retrieved from Internet URL: http://www2.basf.us/pc_textiles/pdfs/CyclanonECO.pdf.
Schrader, K., "Basics and recipes of cosmetics", Second Improved and Extended Edition, 1989, Huethig Buch Verlag, Heidelberg, Germany.

* cited by examiner

Primary Examiner — Eisa B Elhilo
(74) Attorney, Agent, or Firm — Lorenz & Kopf, LLP

(57) ABSTRACT

Agents for the reductive decolorization of dyed keratin fibers contain, in a cosmetic carrier, (a) at least one compound of formula (I), $A[(CR^1R^2)SO_2M]_{p,q}$ (I), in which A represents $N(R^3)_{3-q}$ or $O(R^4)_{2-p}$, $R^1$, $R^2$, $R^4$ represent a hydrogen atom or a $C^1$-$C^6$ alkyl group, $R^3$ represents residues selected from the group of a hydrogen atom, a $C_1$-$C_{20}$ alkyl group, a $C_3$-$C_8$ cycloalkyl group optionally substituted with one to three $C_1$-$C_4$ alkyl residues, M represents residues selected from a hydrogen atom or an equivalent of an alkali metal ion, alkaline-earth metal ion, or metal ion, p represents 1 or 2, q represents 1, 2, or 3, wherein at least one of $R^1$, $R^2$, $R^4$ represents a $C_1$-$C_6$ alkyl group if A represents $O(R^4_{2-p})$, and $R^3$ does not represent a hydrogen atom if q equals 1, and (b) optionally at least one compound of formula (II), $A[(CR^1R^2)SO_3M]_{p,q}$ (II).

20 Claims, No Drawings

DECOLORIZATION OF DYED KERATIN FIBERS

CROSS-REFERENCE TO RELATED APPLICATION

This application is a U.S. National-Stage entry under 35 U.S.C. § 371 based on International Application No. PCT/EP2015/075785, filed Nov. 5, 2015 which was published under PCT Article 21(2) and which claims priority to German Application No. 102014225545.7, filed Dec. 11, 2014, which are all hereby incorporated by reference in their entirety.

TECHNICAL FIELD

The present disclosure comes from the field of cosmetics and relates to compositions for the reductive decolorization of dyed keratin fibers, in particular human hair, containing, in a cosmetic carrier, at least one sulfinic acid derivative of formula (I) as well as, optionally, at least one sulfinic acid derivative of formula (II). An additional object of the present disclosure concerns multi-component packaging units (kit of parts), by way of which the aforementioned compositions are able to be produced. A third object of the present disclosure concerns a method for the coloration and decolorization of keratin fibers, in particular human hair.

BACKGROUND

Preparations for tinting and coloring hair are an important type of cosmetic product. They can be used to lighten or darken the natural shade of hair color according to the wishes of the particular user, to obtain a completely different color, or to cover unwanted color tones, for example grays. Depending on the color or the duration of the coloration desired, conventional hair colorants are formulated either on the basis of oxidation dyes or on the basis of substantive dyes. In many cases, combinations of oxidation dyes and substantive dyes are also used to obtain special shades.

Colorants based on oxidation dyes lead to brilliant and long-lasting colors. However, they do involve the use of strong oxidizing agents, for example hydrogen peroxide solutions. Dyes of this kind contain oxidation dye precursors, so-called developer components as well as coupler components. Under the influence of oxidation agents or atmospheric oxygen, the developer components form the actual dyes together with one another or by coupling with one or more coupling components.

Colorants based on substantive dyes are frequently used for temporary colors. Substantive dyes are based on dye molecules which are directly absorbed onto the hair and do not require an oxidative process for developing the color. Important representatives of this class of dyes include triphenylmethane dyes, azo dyes, anthraquinone dyes or nitrobenzene dyes, each of which can bear both cationic or anionic groups.

In the course of the colorization processes, it can for a variety of reasons be the case that the colorization must be partially or completely reversed. For example, a partial removal of the colorization becomes appropriate if the resulting color of the fibers is darker than desired.

On the other hand, a complete removal of the coloring may be desirable in some cases. For example, it is conceivable that hair will be dyed or tinted for a certain occasion, but is intended to return to its original color after several days.

Methods for color removal are already known in the literature. One method well-known from the prior of art for the reversal of colorizations is an oxidative process for after-treating the dyed hair, for example with the aid of a conventional bleaching agent. During this process, however, the fibers can become damaged due to the introduction of strong oxidizing agents.

Furthermore, reductive processes for the removal of color have already been described. For example, European Patent Application EP 1 300 136 A2 discloses a method for hair treatment in which the hair is colored in a first step and the color reductively removed in a second step. The reductive decolorization thereby is effected by applying a formulation containing a dithionic salt and a surfactant. In WO 2008/055756 A2, the reductive decolorization is performed using a mixture of a reducing agent and an absorbing agent.

The decolorization occurs by using reductive decolorization agents to reduce the dyes found on the keratin fibers or hair. Due to the reduction, the dyes are normally transformed into their reduced leuco forms. During this process, the double bonds present in the dyes are reduced in such a way that the chromophore system of the dyes is interrupted, and the dye is converted to a colorless form.

An overall problem with the reductive decolorization agents known from the prior art is that, although the color can initially be removed from the dyed keratin fibers through the use of the reducing agent, the color removal is not permanent. In some cases, realistic and high-quality colorizations are achieved with hair that has been dyed in an oxidative process whereby the coloration is generated in the hair using oxidation dye precursors of the developer type and the coupler type. However, by applying the reductive decolorization agent, these dyes are then reductively transformed into colorless compounds, which, by virtue of their authenticity and high-quality, continue to remain on the hair.

After the reducing agent has been rinsed away, these reduced forms can gradually be reoxidized under the influence of atmospheric oxygen. As a result of this reoxidation, a more or less pronounced recoloration takes place. This recoloration does not usually correspond to the shade with which the keratin fibers had previously been dyed, and may turn out to be unexpectedly unattractive, thus less than desirable to the user of the decolorization agent.

BRIEF SUMMARY

Agents, multi-component packaging units, and methods for the reductive decolorization of dyed keratin fibers, in particular human hair, are provided herein. In an embodiment, an agent includes, in a cosmetic carrier, (a) at least one compound of formula (I)

$$A[(CR^1R^2)SO_2M]p,q \qquad (I)$$

in which A represents $N(R^3R)_{3-q}$ or $O(R^4)_{2-p}$, $R^1$, $R^2$, $R^4$ independently of one another represent a hydrogen atom or a $C_1C_6$-alkyl group, $R^3$ represents identical or different residues selected from the group of a hydrogen atom, a $C_1$-$C_{20}$-alkyl group, and a $C_3$-$C_8$-cycloalkyl group optionally substituted with one to three $C_1$-$C_4$-alkyl residues, M represents identical or different residues selected from a hydrogen atom or an equivalent of an alkali metal ion, alkaline earth metal ion, or metal ion, p represents the numbers 1 or 2, q represents the numbers 1, 2, or 3, wherein at least one of the residues $R^1$, $R^2$, $R^4$ represents a $C_1$-$C_6$-alkyl group if A represents $O(R^4_{2-p})$, and wherein $R^3$ does not represent a hydrogen atom if q equals 1. The agent also optionally includes (b) at least one compound of formula (II)

$$A[(CR^1R^2)SO_3M]_{p,q} \quad (II)$$

wherein A, $R^1$, $R^2$, $R^3$, $R^4$, M, p and q have the same general meaning as in formula (I), wherein the selection of these variables does not have to be the same for the compounds of formulas (I) and (II) in the specific individual case.

In another embodiment, a multi-component packaging unit (kit of parts) for the reductive decolorization of dyed keratin fibers, includes at least two separately fabricated preparations (A) and (B). The first preparation (A) includes, in a cosmetic carrier, (a) at least one compound of formula (I)

$$A[(CR^1R^2)SO_2M]_{p,q} \quad (I)$$

in which A represents $N(R^3)_{3-q}$ or $O(R^4)_{2-p}$, $R^1$, $R^2$, $R^4$ independently of one another represent a hydrogen atom or a $C_1$-$C_6$-alkyl group, $R^3$ represents identical or different residues selected from the group of a hydrogen atom, a $C_1$-$C_{20}$-alkyl group, and a $C_3$-$C_8$-cycloalkyl group optionally substituted with one to three $C_1$-$C_4$-alkyl residues, M represents identical or different residues selected from a hydrogen atom or an equivalent of an alkali metal ion, alkaline earth metal ion, or metal ion, p represents the numbers 1 or 2, q represents the numbers 1, 2, or 3, wherein at least one of the residues $R^1$, $R^2$, $R^4$ represents a $C_1$-$C_6$-alkyl group if A represents $O(R^4_{2-p})$, and wherein $R^3$ does not represent a hydrogen atom if q equals 1. The first preparation (A) also optionally includes (b) at least one compound of formula (II)

$$A[(CR^1R^2)SO_3M]_{p,q} \quad (II)$$

wherein A, $R^1$, $R^2$, $R^3$, $R^4$, M, p and q have the same general meaning as in formula (I), wherein the selection of these variables does not have to be the same for the compounds of formulas (I) and (II) in the specific individual case. The second preparation (B)—based on the total weight of preparation (B)—has a water content of from about 5.0 to about 99.0% by weight, includes at least one inorganic and/or one organic acid, and has a pH value in the range of from about 0 to about 4.5.

In another embodiment, a method for the coloration and reductive decolorization of keratin fibers, in particular human hair, includes the following steps and in the sequence specified: (I) applying a cosmetic dye including at least one substantive dye and/or at least one oxidative dye precursor to the keratin fibers, (II) allowing the dye to act for a period of from about 5 to about 60 minutes, (III) rinsing out the dye, (IV) applying a decolorization agent to the keratin fibers, wherein the agent includes, in a cosmetic carrier, (a) at least one compound of formula (I)

$$A[(CR^1R^2)SO_2M]_{p,q} \quad (I)$$

in which A represents $N(R^3)_{3-q}$ or $O(R^4)_{2-p}$, $R^1$, $R^2$, $R^4$ independently of one another represent a hydrogen atom or a $C_1C_6$-alkyl group, $R^3$ represents identical or different residues selected from the group of a hydrogen atom, a $C_1$-$C_{20}$-alkyl group, and a $C_3$-$C_8$-cycloalkyl group optionally substituted with one to three $C_1$-$C_4$-alkyl residues, M represents identical or different residues selected from a hydrogen atom or an equivalent of an alkali metal ion, alkaline earth metal ion, or metal ion, p represents the numbers 1 or 2, q represents the numbers 1, 2, or 3, wherein at least one of the residues $R^1$, $R^2$, $R^4$ represents a $C_1$-$C_6$-alkyl group if A represents $O(R^4_{2-p})$, and wherein $R^3$ does not represent a hydrogen atom if q equals 1. Optionally, the agent further includes (b) at least one compound of formula (II)

$$A[(CR^1R^2)SO_3M]_{p,q} \quad (II)$$

wherein A, $R^1$, $R^2$, $R^3$, $R^4$, M, p and q have the same general meaning as in formula (I), wherein the selection of these variables does not have to be the same for the compounds of formulas (I) and (II) in the specific individual case. The method proceeds with (V) allowing the decolorization agent to act at from about 20 to about 45° C. for a period of from about 5 to about 60 minutes, (VI) rinsing out the decolorization agent, and (VII) optionally, applying an after-treatment agent to the keratin fibers, wherein the after-treatment agent includes at least one surfactant chosen from the group of anionic, cationic, nonionic amphoteric, and/or zwitterionic surfactants.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Therefore, the object of the present disclosure is to provide a decolorization agent for decolorizing dyed keratin fibers that removes the coloration from dyed keratin fibers as completely as possible. The decolorization should be long-lasting, and, under the influence of atmospheric oxygen, the decolorized keratin fibers should suffer no recoloring, no shift in shading, and no subsequent darkening. The decolorization agent should demonstrate good performance in decolorizing keratin fibers, particularly those previously dyed using oxidative colorants based on oxidation dye precursors of the developer and the coupler type. In addition, the decolorization agent should be toxicologically harmless.

In the course of the work leading to the present disclosure, it has been found that said object can be achieved by the use of decolorization agents which contain, in a cosmetic carrier, one or more sulfinic acid derivatives corresponding to formula (I) as described below.

For example, processes for the reductive after-treatment of polyester textiles using sulfinic acid derivatives of formula (I) are known from EP 0 914 516 B1. During the after-treatment of the polyester textiles, however, the sulfinic acid derivatives of formula (I) are employed solely under conditions barely acceptable for cosmetics, meaning temperatures of from about 50-100° C. It has now been found that these sulfinic acid derivatives are also suitable for decolorizing keratin fibers or human hair when the keratin fibers have been previously colored with substantive dyes and/or oxidation dye precursors (developers and couplers). Particularly surprising in this context was the fact that the decolorization of the keratin fibers even took place under physiologically acceptable conditions, meaning at temperatures less than about 45° C.

A first object of the present disclosure is an agent for the reductive decolorization of colored keratin fibers, in particular human hair, containing, in a cosmetic carrier (a) at least one compound of formula (I)

$$A[(CR^1R^2)SO_2M]_{p,q} \quad (I)$$

in which
A represents $N(R^3)_{3-q}$ or $O(R^4)_{2-p}$
$R^1$, $R^2$, $R^4$ independently of one another represent a hydrogen atom or a $C_1$-$C_6$-alkyl group $R^3$ represents identical or different residues selected from the group consisting of a hydrogen atom, a $C_1$-$C_{20}$-alkyl group, a $C_3$-$C_8$-cycloalkyl group optionally substituted with one to three $C_1$-$C_4$-alkyl residues M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion (NH4+)

p represents the numbers 1 or 2,
q represents the numbers 1, 2, or 3,
wherein
at least one of the residues $R^1$, $R^2$, $R^4$ represents a $C_1$-$C_6$-alkyl group if A represents $O(R^4_{2-p})$, and
$R^3$ does not represent a hydrogen atom if q equals 1,
and
(b) optionally at least one compound of formula (II)

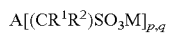

wherein A, $R^1$, $R^2$, $R^3$, $R^4$, M, p and q have the same general meaning as in formula (I), whereby the selection of these variables does not have to be the same for the compounds of formulas (I) and (II) in the specific individual case.

Depending on the choice of colorants previously used to dye the hair, the application of the decolorization agent as contemplated herein achieves a nearly complete or an actually complete decolorization of previously dyed keratin fibers. The decolorization agent as contemplated herein demonstrates an especially outstanding effect on keratin fibers that were previously colored with oxidation colorants.

It was particularly surprising to find that this decolorization effect persists even after the reducing agent has been rinsed out, and that, after some hours or days of exposure to the influence of atmosphere oxygen, the colored keratin fibers are barely affected by reoxidation and darkening.

Keratin fibers are to be understood as firs, wool, feathers, and in particular human hair. Although the agents according to the present disclosure are suitable principally for decolorizing keratin fibers or human hair, nothing in principle conflicts with use in other fields as well.

The term "colored keratin fibers" is understood to mean keratin fibers which have been colored using conventional cosmetic colorants known to those skilled in the art.

The term "colored keratin fibers" is understood in particular to mean keratin fibers which have been colored using oxidative dyes (developers and couplers) known from the prior art. Reference is specifically made in this context to the known works which reproduce the relevant knowledge of one skilled in the art, for example by Kh. Schrader, Grundlagen und Rezepturen der Kosmetika [Fundamentals and Formulations of Cosmetics], 2nd ed., Hiithig Buch Verlag, Heidelberg, 1989. In each case, the agents contain the ingredients relevant to the present disclosure in a cosmetic carrier, for example in a suitable aqueous or aqueous alcoholic carrier.

For the purpose of reductive decolorization, carriers of this kind may be, for example, creams, emulsions, gels as well as surfactant-containing foaming solutions, for example shampoos, foam aerosols, foam formulations, or other preparations suitable for application to the hair. It is particularly preferable that the agents for the reductive removal of color from keratin fibers be creams, emulsions or flowable gels.

The decolorizing agents contain as ingredients relevant to the present disclosure at least one sulfinic acid derivative of formula (I)

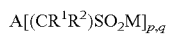          (I)

in which
A represents $N(R^3)_{3-q}$ or $O(R^4)_{2-p}$
$R^1$, $R^2$, $R^4$ independently of one another represent a hydrogen atom or a $C_1$-$C_6$-alkyl group
$R^3$ represents identical or different residues selected from the group consisting of a hydrogen atom, a $C_1$-$C_{20}$-alkyl group, a $C_3$-$C_8$-cycloalkyl group optionally substituted with one to three $C_1$-$C_4$-alkyl residues M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion ($NH_4^+$)

p represents the numbers 1 or 2,
q represents the numbers 1, 2, or 3,
wherein
at least one of the residues $R^1$, $R^2$, $R^4$ represents a $C_1$-$C_6$-alkyl group if A represents $O(R^4_{2-p})$, and
$R^3$ does not represent a hydrogen atom if q equals 1, Exemplary substituents $R^1$ to $R^4$ of the compounds in formula (I) are explained as follows: Exemplary $C_1$-$C_6$-alkyl groups are the methyl, ethyl, propyl, isopropyl, n-butyl, s-butyl, and t-butyl, n-pentyl and n-hexyl groups. Preferred alkyl residues are propyl, methyl and ethyl. Exemplary $C_7$-$C_{20}$-alkyl groups are the n-octyl, the n-decyl, the n-dodecyl, the n-tetradecyl, the n-hexadecyl, and the n-octadecyl groups. Exemplary $C_3$-$C_6$-cycloalkyl groups can be specified as the cyclopropyl group, the cyclopentyl group, or the cyclohexyl group.

The residue A in formula (I) can represent either a grouping $N(R^3)^{3-q}$ or for a grouping $O(R^4)_{2-p}$. Depending on whether A represents a grouping $N(R^3)_{3-q}$ or a grouping $O(R^4)_{2-p}$, either the number p or the number q is to be used in formula (I).

If A represents the grouping $N(R^3)_{3-q}$, then the sulfinic acid derivative as contemplated herein is a compound corresponding to formula (Ia)

          (Ia)

Therefore, given A equal to $N(R^3)_{3-q}$, of concern here is the formula $N(R^3)_{3-q}[(CR^1R^2)SO_2M]_q$. If A represents the grouping $O(R^4)_{2-p}$ then the sulfinic acid derivative as contemplated herein is a compound of formula (Ib)

          (Ib)

Given A equal to $O(R^4)_{2-p}$ of concern here is the formula $O(R^4)_{2-p}[(CR^1R^2)SO_2M]p$ The residue p in formula (I) can represent the numbers 1 or 2.

If A represents the number 1, then the sulfinic acid derivative as contemplated herein is a compound of formula $O(R^4)_1[(CR^1R^2)SO_2M]_1$.

If A represents the number 2, then the sulfinic acid derivative as contemplated herein is a compound of formula $O[(CR^1R^2)SO_2M]_2$.

The stipulation applies in this regard that at least one of the residues $R^1$, $R^2$, $R^4$ represents a $C_1$-$C_6$-alkyl group when A represents $O(R^4_{2-p})$.

Thus, in both of the formulas $O(R^4)_1_1[(CR^1R^2)SO_2M]_1$ and $O[(CR^1R^2)SO_2M]_2$, at least one of the residues from the group consisting of $R^1$, $R^2$, and $R^4$ represents a $C_1$-$C_6$-alkyl group.

The best decolorization results can be achieved by using a compound of formula (Ia). Consequently, it is particularly preferable if the agent as contemplated herein contains at least one compound of formula (Ia), hence at least $N(R^3)_{3-q}[(CR^1R_2)SO_2M]_q$ compound.

In a particularly preferential embodiment, an agent as contemplated herein contains as (a) at least one compound of formula (Ia), $$A[(CR^1R^2)SO_2M]_q \qquad (Ia)$$

in which
A represents $N(R^3)_{3-q}$
The residue q can represent the numbers 1, 2, or 3.
If q represents the number 1, then the sulfinic acid derivative as contemplated herein is a compound of formula $N(R_3)_2[(CR^1R^2)SO_2M]_1$.
If A represents the number 2, then the sulfinic acid derivative as contemplated herein is a compound of formula $N(R^3)_1[(CR^1R^2)SO_2M]_2$.
If q represents the number 3, then the sulfinic acid derivative as contemplated herein is a compound of formula $N[(CR^1R^2)SO_2M]_3$.

The stipulation applies in this regard that $R^3$ does not represent a hydrogen atom if q equals 1, which means that, in the formula $N(R^3)_2[(CR^1R^2)SO_2M]_1$, the residue R3 cannot represent a hydrogen atom.

It is preferable for q to represent the number 2 or 3; in a quite particularly preferable embodiment, q represents the number 3.

In a particularly preferential embodiment, an agent as contemplated herein contains as (a) at least one compound of formula (Ia), in which
q represents the numbers 2 or 3, preferably the number 3.

The residuals R1 and R2, independently of one another, represent a hydrogen atom or a $C_1$-$C_6$-alkyl group. With respect to the solution of the problem posed in terms of the present disclosure, it is furthermore particularly preferable if, independently of one another, R1 and R2 represent a hydrogen atom or a methyl group. Most preferably, the residuals R1 and R2 both represent a hydrogen atom.

In an additional particularly preferential embodiment, an agent as contemplated herein contains as (a) at least one compound of formula (I), in which,
R1 and R2 independently of one another represent a hydrogen atom or a methyl group, preferably a hydrogen atom.

The residual M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion ($NH_4^+$)

The sulfinic acid derivatives as contemplated herein are compounds each possessing—bound to a nitrogen atom or to an oxygen atom—one or more structural —$(CR^1R^2)SO_2M$ units. These structural units are the sulfinomethyl groups substituted with the R1 and R2 residues, which can alternatively be called methanesulfinic acid groups. The sulfinic acid in each of these structural units can be present in protonated form, in which case M represents a hydrogen atom. However, the sulfinic acid can also be present in the form of its salt, preferably its sodium salt, potassium salt, or zinc salt.

In cases where the sulfinic acid derivative as contemplated herein bears several structural $(CR^1R^2)SO_2M$ units, one sulfinic acid unit can be present in protonated form (with M equal to hydrogen), while another (or the additional) sulfinic acid units are present in the form of their salts (with M equal to an equivalent of an alkali metal ion, alkaline earth metal ion, metal ion or ammonium ion).

If the sulfinic acid derivative as contemplated herein is present dissolved in an (optionally aqueous) cosmetic carrier, then the protonated forms of the sulfinic acids are in equilibrium with the deprotonated sulfinic acids, and all of these forms are thus explicitly included in the present disclosure.

The residual M quite preferably represents identical or different residues selected from a hydrogen atom or an equivalent of an alkali metal ion, alkaline earth metal ion or metal ion from the group consisting of sodium, potassium, and ½ zinc.

In an additional particularly preferential embodiment, an agent as contemplated herein contains as (a) at least one compound of formula (I), in which
M represents identical or different residues selected from a hydrogen atom or an equivalent of an alkali metal ion, alkaline earth metal ion, or metal ion from the group consisting of sodium, potassium, and ½ zinc.

As a result of synthesis, the production of the compounds in formula (I) can also lead to the occurrence of varying proportions of the compounds in formula (II), which may likewise potentially be contained in the agents as contemplated herein.

Therefore, the agents for the reductive decolorization of dyed keratin fibers may optionally also (b) contain at least one compound of formula (II)

$$A[(CR^1R^2)SO_3M]_{p,q} \qquad (II)$$

The residues A, $R^1$, $R^2$, $R^3$, $R^4$, M, p and q have the same general meaning as in formula (I), whereby the selection of these variables does not have to be the same for the compounds corresponding to formulas (I) and (II) in the specific individual case.

Exemplary substituents $R^1$ to $R^4$ of the compounds in formula (I) are explained as follows:
Exemplary $C_1$-$C_6$-alkyl groups are the methyl, ethyl, propyl, isopropyl, n-butyl, s-butyl, and t-butyl, n-pentyl and n-hexyl groups. Preferred alkyl residues are propyl, methyl and ethyl. Exemplary $C_7$-$C_{20}$-alkyl groups are the n-octyl, n-decyl, the n-dodecyl, the n-tetradecyl, the n-hexadecyl, and the n-octadecyl groups. Exemplary C3-C6-cycloalkyl groups can be specified as the cyclopropyl group, the cyclopentyl group, or the cyclohexyl group. The residue A in formula (II) can represent either a grouping $N(R^3)_{3-q}$ or a grouping $O(R^4)_{2-p}$. Depending on whether A represents a grouping $N(R^3)_{3-q}$ or a grouping $O(R^4)_{2-p}$, either the number p or the number q is to be used in formula (IIa).

If A represents the grouping $N(R^3)_{3-q}$ then the sulfinic acid derivative as contemplated herein is a compound corresponding to formula (IIa)

$$A[(CR^1R^2)SO_3M]_q \qquad (IIa)$$

Therefore, given A equal to $N(R^3)_{3-q}$, of concern here is the formula $N(R^3)_{3-q}[(CR^1R^2)SO_3M]_q$.
The residue q can represent the numbers 1, 2, or 3.
If q represents the number 1, then the sulfinic acid derivative as contemplated herein is a compound corresponding to formula $N(R^3)_2[(CR^1R^2)SO_3M]_1$.
If q represents the number 2, then the sulfinic acid derivative as contemplated herein is a compound corresponding to formula $N(R^3)_1[(CR^1R^2)SO_3M]_2$.
If q represents the number 3, then the sulfinic acid derivative as contemplated herein is a compound of formula $N[(CR^1R^2)SO_3M]_3$.
The stipulation applies in this regard that $R^3$ does not represent a hydrogen atom if q equals 1, which means that, in the formula $N(R^3)_2[(CR^1R^2)SO_3M]_1$, the residue R3, which is present twice, cannot represent a hydrogen atom.

If A represents the grouping $O(R^4)_{2-p}$ then the sulfinic acid derivative as contemplated herein is a compound of formula (IIb)

$$A[(CR^1R^2)SO_3M]_p \qquad (IIb)$$

in which

Given A equal to $O(R^4)_{2-p}$, of concern here is the formula $O(R^4)_{2-p}[(CR^1R^2)SO_3M]_p$.

The residue p in formula (II) can represent the numbers 1 or 2.

If p represents the number 1, then the sulfinic acid derivative as contemplated herein is a compound of formula $O(R^4)_1[(CR^1R^2)SO_3M]_1$.

If p represents the number 2, then the sulfinic acid derivative as contemplated herein is a compound of formula $O[(CR^1R^2)SO_3M]_2$.

Again, the stipulation applies in this regard that at least one of the residues $R^1$, $R^2$, $R^4$ represents a $C_1$-$C_6$-alkyl group if A represents $O(R^4_{2-p})$.

Thus, in both of the formulas $O(R^4)_1[(CR^1R^2)SO_3M]_1$ and $O[(CR^1R^2)SO_3M]_2$, at least one of the residues from the group consisting of $R^1$, $R^2$ and $R^4$ represents a $C_1$-$C_6$-alkyl group.

The residual M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion ($NH_4^+$)

In a preferential embodiment, an agent for the reductive decolorization of colored keratin fibers, in particular human hair, contains, in a cosmetic carrier, (a) at least one compound of formula (I)

$$A[(CR^1R^2)SO_2M]_{p,q} \qquad (I)$$

in which

A represents $N(R^3)_{3-q}$ or $O(R^4)_{2-p}$ $R^1$, $R^2$, $R^4$ independently of one another represent a hydrogen atom or a $C_1$-$C_6$-alkyl group $R^3$ represents identical or different residues selected from the group consisting of a hydrogen atom, a $C_1$-$C_{20}$-alkyl group, and a $C_3$-$C_8$-cycloalkyl group optionally substituted with one to three $C_1$-$C_4$-alkyl residues M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion ($NH_4^+$)

p represents the numbers 1 or 2, q represents the numbers 1, 2, or 3, wherein at least one of the residues $R^1$, $R^2$, $R^4$ represents a $C_1$-$C_6$-alkyl group if A represents $O(R^4_{2-p})$, and $R^3$ does not represent a hydrogen atom if q equals 1.

In a further preferential embodiment, an agent for the reductive decolorization of colored keratin fibers, in particular human hair, contains, in a cosmetic carrier, (a) at least one compound of formula (I)

$$A[(CR^1R^2)SO_2M]_{p,q} \qquad (I)$$

in which

A represents $N(R^3)_{3-q}$ or $O(R^4)_{2-p}$ $R^1$, $R^2$, $R^4$ independently of one another represent a hydrogen atom or a $C_1$-$C_6$-alkyl group $R^3$ represents identical or different residues selected from the group consisting of a hydrogen atom, a $C_1$-$C_{20}$-alkyl group, and a $C_3$-$C_8$-cycloalkyl group optionally substituted with one to three $C_1$-$C_4$-alkyl residues M represents identical or different residues selected from a hydrogen atom or an equivalent of an alkali metal ion, alkaline earth metal ion, or metal ion, preferably sodium, potassium, ½ magnesium, ½ calcium, ½ zinc, or an ammonium ion ($NH_4^+$)

p represents the numbers 1 or 2, q represents the numbers 1, 2, or 3, wherein at least one of the residues $R^1$, $R^2$, $R^4$ represents a $C_1$-$C_6$-alkyl group if A represents $O(R^4_{2-p})$, and $R^3$ does not represent a hydrogen atom if q equals 1, and (b) at least one compound of formula (II)

$$A[(CR^1R^2)SO_3M]p,q \qquad (II)$$

wherein A, $R^1$, $R^2$, $R^3$, $R^4$, M, p and q have the same general meaning as in formula (I), wherein the selection of these variables does not have to be the same for the compounds of formulas (I) and (II) in the specific individual case.

If the reductive decolorization agents as contemplated herein contain both a compound of formula (I) and a compound of formula (II), it is advantageous for the compounds of formulas (I) and (II) to be introduced in specific proportions relative to one another. A preferable molar ratio in this context is from about 20:1 to about 1:20, more preferably from about 10:1 to about 1:10, and most preferably from about 3:1 to about 1:3. Therefore, the molar ratio of all the compounds of formula (I) contained in the agent to all of the compounds of formula (II) contained in the agent, thus the molar ratio of (I)/(II), preferably has a value of from about 20:1 to about 1:20, more preferably a value of from about 10:1 to about 1:10, and most preferably from about 3:1 to about 1:3.

In a further embodiment, an agent as contemplated herein has a molar ratio of all compounds of formula (I) contained in the agent to all the compounds of formula (II) contained in the agent, thus the molar ratio of (I)/(II), has a value of from about 20:1 to about 1:20, more preferably a value of from about 10:1 to about 1:10, and most preferably from about 3:1 to about 1:3.

Certain compounds of formula (I) are able to achieve an especially good decolorization result for oxidatively dyed hair. Therefore, particular preference is given to the use of one or more compounds from the group consisting of $HN(CH_2SO_2Na)_2$, disodium[(sulfinatomethyl)amino]methanesulfinate $HN(CH_2SO_2K)_2$, disodium[(sulfinatomethyl)amino]methanesulfinate $HN(CH_2SO_2H)_2$, [(sulfinomethyl)amino]methanesulfinic acid $N(CH_2SO_2Na)_3$, trisodium[bis(sulfinatomethyl)amino]methanesulfinate $N(CH_2SO_2K)_3$, tripotassium[bis(sulfinatomethyl)amino]methanesulfinate $N(CH_2SO_2H)_3$, [bis(sulfinomethyl)amino]methanesulfinic acid $H_2NCH(CH_3)SO_2Na$, sodium 1-aminoethane-1-sulfinate $H_2NCH(CH_3)SO_2K$, potassium 1-aminoethane-1-sulfinate $H_2NCH(CH_3)SO_2H$, 1-aminoethane-1-sulfinic acid, $HN(CH(CH_3)SO_2Na)_2$, disodium 1-[(1-sulfinatoethyl)amino]ethane-1-sulfinate $HN(CH(CH_3)SO_2K)_2$, dipotassium 1-[(1-sulfinatoethyl)amino]ethane-1-sulfinate $HN(CH(CH_3)SO_2H)_2$, 1-[(1-sulfinoethyl)amino]ethane-1-sulfinic acid $N(CH(CH_3)SO_2Ha_3$, trisodium 1-[bis(1-sulfinatoethyl)amino]ethane-1-sulfinate and/or N(CH(CH₃)SO₂K)₃, tripotassium 1-[bis(1-sulfinatoethyl)amino]ethane-1-sulinate N(CH(CH₃)SO₂H)₃, 1-[bis(1-sulfinoethyl)amino]ethane-1-sulfinic acid In a particularly preferential embodiment, an agent as contemplated herein contains as (a) at least one compound of formula (I), which is selected from the group consisting of HN(CH₂SO₂Na)₂, trisodium[(sulfinatomethyl)amino]methanesulfinate HN(CH₂SO₂K)₂, dipotassium[(sulfinatomethyl)amino]methanesulfinate HN(CH₂SO₂H)₂, [(sulfinomethyl)amino]methanesulfinic acid N(CH₂SO₂Na)₃, trisodium[bis(sulfinatomethyl)amino]methanesulfinate N(CH₂SO₂K)₃, tripotassium[bis(sulfinatomethyl)amino]methanesulfinate N(CH₂SO₂H)₃, [bis(sulfinomethyl)amino]methanesulfinsäure H₂NCH(CH₃)SO₂Na, sodium 1-aminoethane-1-sulfinate H₂NCH(CH₃)SO₂K, potassium 1-aminoethane-1-sulfinate H₂NCH(CH₃)SO₂H, 1-aminoethane-1-sulfinic acid, HN(CH(CH₃)SO₂Na)₂, disodium 1-[(1-sulfinatoethyl)amino]ethane-1-sulfinate HN(CH(CH₃)SO₂K)₂, dipotassium 1-[(1-sulfinatoethyl)amino]ethane-1-sulfinate HN(CH(CH₃)SO₂H)₂, 1-[(1-sulfinoethyl)amino]ethane-1-sulfinic acid N(CH(CH₃)SO₂Na)₃, trisodium 1-[bis(1-sulfinatoethyl)amino]ethane-1-sulfinate and/or N(CH(CH₃)SO₂K)₃, tripotassium 1-[bis(1-sulfinatoethyl)amino]ethane-1-sulinate and/or N(CH(CH₃)SO₂H)₃, 1-[bis(1-sulfinoethyl)amino]ethane-1-sulfinic acid.

The compounds of formula (II) optionally contained in the agents as contemplated herein are also preferably selected from a specific group of compounds. Therefore, particular preference is given to the use of one or more compounds from the group consisting of HN(CH₂SO₃Na)₂, disodium[(sulfonatomethyl)amino]methanesulfonate HN(CH₂SO₃K)₂, dipotassium[(sulfonatomethyl)amino]methanesulfonate HN(CH₂SO₃H)₂, [sulfomethyl)amino]methanesulfonic acid N(CH₂SO₃Na)₃, trisodium[bis(sulfonatomethyl)amino]methanesulfonate N(CH₂SO₃K)₃, tripotassium[bis(sulfonatomethyl)amino]methanesulfonate N(CH₂SO₃H)₃, [bis(sulfomethyl)amino]methanesulfonic acid H₂NCH(CH₃)SO₃Na, sodium 1-aminoethane-1-sulfonate H₂NCH(CH₃)SO₃K, potassium 1-aminoethane-1-sulfonate H₂NCH(CH₃)SO₃H, 1-aminoethane-1-sulfonic acid, HN(CH(CH₃)SO₃Na)₂, disodium 1-[(1-sulfonatoethyl)amino]ethane-1-sulfonate HN(CH(CH₃)SO₃K)₂, dipotassium 1-[(1-sulfonatoethyl)amino]ethane-1-sulfonate HN(CH(CH₃SO₃H)₂, 1-[(1-fulfoethyl)amino]ethane-1-sulfonic acid N(CH(CH₃)SO₃Na)₃, trisodium 1-[bis(1-sulfonatoethyl)amino]ethane-1-sulfonate N(CH(CH₃)SO₃K)₃, tripotassium 1-[bis(1-sulfonatoethyl)amino]ethane-1-sulfonate N(CH(CH₃)SO₃H)₃, 1-[bis(1-sulfoethyl)amino]ethane-1-sulfonic acid In a particularly preferential embodiment, an agent as contemplated herein contains as (b) at least one compound of formula (II), which is selected from the group consisting of HN(CH₂SO₃Na)₂, disodium[(sulfonatomethyl)amino]methanesulfonate HN(CH₂SO₃K)₂, dipotassium[(sulfonatomethyl)amino]methanesulfonate HN(CH₂SO₃H)₂, [sulfomethyl)amino]methanesulfonic acid N(CH₂SO₃Na)₃, trisodium[bis(sulfonatomethyl)amino]methanesulfonate N(CH₂SO₃K)₃, tripotassium[bis(sulfonatomethyl)amino]methanesulfonate N(CH₂SO₃H)₃, [bis(sulfomethyl)amino]methanesulfonic acid H₂NCH(CH₃)SO₃Na, sodium 1-aminoethane-1-sulfonate H₂NCH(CH₃)SO₃K, potassium 1-aminoethane-1-sulfonate H₂NCH(CH₃)SO₃H, 1-aminoethane-1-sulfonic acid, HN(CH(CH₃)SO₃Na)₂, disodium 1-[(1-sulfonatoethyl)amino]ethane-1-sulfonate HN(CH(CH₃)SO₃K)₂, dipotassium 1-[(1-sulfonatoethyl)amino]ethane-1-sulfonate HN(CH(CH₃)SO₃H)₂, 1-[(1-sulfoethyl)amino]ethane-1-sulfonic acid.

N(CH(CH₃(SO₃Na)₃, trisodium 1-[bis(1-sulfonatoethyl)amino]ethane-1-sulfonate

N(CH(CH₃)SO₃K)₃, tripotassium 1-[bis(1-sulfonatoethyl)amino]ethane-1-sulfonate and/or N(CH(CH₃)SO₃H)₃, 1-[bis(1-sulfoethyl)amino]ethane-1-sulfonic acid The reducing agent(s) of formula (I) are preferably introduced in certain proportions. A decolorization effect can be observed even with small quantities. However, in order to achieve a sufficient and strong decolorization effect, it is advantageous if the decolorization agent contains one or more reducing agents of formula (I) in a total quantity of from about 0.1 to about 30.0% by weight, preferably of from about 0.2 to about 20.0% by weight, more preferably of from about 0.3 to about 10.0% by weight, and most preferably of from about 0.5 to about 6.0% by weight. The basis for calculating the quantities specified in % by weight in this regard is the total weight of all the reducing agents of formula (I) contained in the agent compared to the total weight of the agent.

In a further particularly preferential embodiment, an agent as contemplated herein contains—based on the total weight of the agent—one or more compounds of formula (I) in a total quantity of from about 0.1 to about 30.0% by weight, preferably of from about 0.2 to about 20.0% by weight, more preferably of from about 0.3 to about 10.0% by weight, and most preferably of from about 0.5 to about 6.0% by weight.

The compounds of formula (II) optionally contained in the agents are also preferably introduced in certain proportions. It is advantageous if the decolorization agent contains one or more compound(s) of formula (II) in a total quantity of from about 0.1 to about 30.0% by weight, preferably of from about 0.2 to about 20.0% by weight, more preferably of from about 0.3 to about 10.0% by weight, and most preferably of from about 0.5 to about 6.0% by weight. The basis for calculating the quantities specified in % by weight in this regard is the total weight of all the compounds of formula (II) contained in the agent compared to the total weight of the agent.

In a further particularly preferential embodiment, an agent as contemplated herein contains—based on the total weight of the agent—one or more compounds of formula (II) in a total quantity of from about 0.1 to about 30.0% by weight, preferably of from about 0.2 to about 20.0% by weight, more preferably of from about 0.3 to about 10.0% by weight, and most preferably of from about 0.5 to about 6.0% by weight.

One particularly preferable reducing agent that contains compounds of formulas (I) and (II) uses as a raw material Cyclanon Clear ECO, which is alternatively referred to as Cyclanon ECO and is commercially available from the BASF company. Cyclanon ECO is a mixture of the compounds $N(CH_2SO_2Na)_3$ und $N(CH_2SO_3Na)_3$ at a molar ratio of 1:1.

Moreover, the agent as contemplated herein can also contain one or more reducing agents (c) from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, sodium disulfite, potassium disulfite, ammonium disulfite, hydroxymethanesulfinic acid, aminomethanesulfinic acid, cysteine, thiolactic acid, thioglycolic acid (alternative name: sulfanylacetic acid), oxalic acid, oxaloacetic acid and/or ascorbic acid.

Sodium dithionite is an inorganic reducing agent of molecular formula $Na_2SO_4$ and CAS no. 7775-14-6.

Zinc dithionite is an inorganic reducing agent of molecular formula $ZnS_2O_4$ and CAS no. 7779-86-4.

Potassium dithionite is an inorganic reducing agent of molecular formula $K_2S_2O_4$ and CAS no. 14293-73-3.

Sodium sulfite is an inorganic reducing agent of molecular formula $Na_2SO_3$ and CAS no. 7757-83-7.

Sodium hydrogen sulfite is an inorganic reducing agent of molecular formula $NaHSO_3$ and CAS no. 7631-90-5.

Sodium hydrogen sulfite is preferably introduced in the form of an aqueous solution.

Potassium sulfite is an inorganic reducing agent of molecular formula $K_2SO_3$ and CAS no. 10117-38-1.

Potassium hydrogen sulfite is an inorganic reducing agent of molecular formula $KHSO_3$ and CAS no. 7773-03-7.

Ammonium sulfite is an inorganic reducing agent of molecular formula $(NH_4)_2SO_3$ and CAS no. 10196-04-0.

Sodium thiosulfate is an inorganic reducing agent of molecular formula $Na_2S_2O_3$ and CAS no. 7772-98-7.

Potassium thiosulfate is an inorganic reducing agent of molecular formula $K_2S_2O_3$ and CAS no. 10294-66-3.

Ammonium thiosulfate is an inorganic reducing agent of molecular formula $(NH_4)_2S_2O_3$ and CAS no. 7783-18-8.

Hydroxymethanesulfinic acid is an inorganic reducing agent of molecular formula $HO-CH_2-S(O)OH$ and CAS no. 79-25-4. Hydroxymethanesulfinic acid is alternatively referred to as formaldehyde-sulfoxylic acid.

As contemplated herein is both the use of hydroxymethanesulfinic acid proper as well as the use of physiologically compatible salts of hydroxymethanesulfinic acid, for example sodium salt and/or zinc salt.

Therefore, the use of sodium formaldehyde sulfoxylate (sodium hydroxymethanesulfinate, the sodium salt of hydroxymethanesulfinic acid) and/or zinc formaldehyde sulfoxylate (zinc hydroxymethanesulfinate, the zinc salt of hydroxymethanesulfinic acid) is also as contemplated herein.

Aminomethanesulfinic acid is an inorganic reducing agent of molecular formula $H_2N-CH_2-S(O)OH$ and CAS no. 118201-33-5. As contemplated herein is both the use of aminomethanesulfinic acid proper as well as the use of physiologically compatible salts of aminomethanesulfinic acid, for example sodium salt and/or zinc salt. Therefore, the use of sodium aminomethanesulfinate (the sodium salt of aminomethanesulfinic acid) and/or zinc aminomethanesulfinate (the zinc salt of aminomethanesulfinic acid) is also as contemplated herein.

In terms of the present disclosure, cysteine (2-amino-3-sulfanylpropanoic acid) is understood to mean D-cysteine, L-cysteine and/or a mixture of D- and L-cysteine.

Thiolactic acid (2-sulfanylpropanoic acid) is understood to mean D-thiolactic acid, L-thiolactic acid and/or a mixture of D- and L-thiolactic acid.

As contemplated herein is both the use of thiolactic acid proper as well as the use of a physiologically compatible salt of thiolactic acid. One preferred salt of thiolactic acid is ammonium thiolactate. Ammonium thiolactate is the ammonium salt of thiolactic acid (meaning the ammonium salt of 2-sulfanylpropanoic acid) (Formula XX).

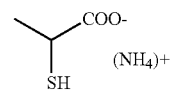

(Formula XX)

Included within the definition of ammonium thiolactate are both the ammonium salts of D-thiolactic acid and the ammonium salts of L-thiolactic acid, and mixtures thereof. Thioglycolic acid (sulfanylacetic acid, 2-mercaptoacetic acid) is understood to be an organic reducing agent of formula $HS-CH_2-COOH$, the compound of which has CAS no. 68-11-1. In regard to thioglycolic acid, both the use of thiolactic acid proper as well as the use of a physiologically compatible salt of thiolactic acid is also as contemplated herein. Suitable physiologically compatible salts of thioglycolic acid are, for example, sodium thioglycolate, potassium thioglycolate and/or ammonium thioglycolate. Ammonium thioglycolate is a preferred physiologically compatible salt of thioglycolic acid.

Ammonium thioglycolate is the ammonium salt of thioglycolic acid (meaning the ammonium salt of sulfanylacetic acid) (Formula XXX).

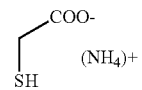

(Formula XXX)

Oxalic acid is understood to be the acid $HOOC-COOH$, which has a reducing effect. Oxalic acid is alternatively referred to as ethanedioic acid, and has CAS no. 144-62-7. Alternate names for oxaloacetic acid are oxobutanedioic acid and oxosuccinic acid; this acid also has a reducing effect, and has CAS no. 328-42-7.

As contemplated herein, ascorbic acid is in particular understood to be (R)-5-[(S)-1,2-dihydroxyethyl]-3,4-dihydroxy-5H-furan-2-one (other alternate names: Vitamin C, L-ascorbic acid) with CAS no. 50-81-7.

Therefore, in a further preferential embodiment, the agent as contemplated herein also contains one or more additional reducing agents (c) from the group of sodium dithionite, zinc dithionite, potassium dithionite, sodium sulfite, sodium hydrogen sulfite, potassium sulfite, potassium hydrogen sulfite, ammonium sulfite, sodium thiosulfate, potassium thiosulfate, ammonium thiosulfate, sodium disulfite, potassium disulfite, ammonium disulfite, hydroxymethanesulfinic acid, aminomethanesulfinic acid, cysteine, thiolactic acid, thioglycolic acid (alternative name: sulfanylacetic acid), and/or ascorbic acid.

The additional reducing agent(s) from the aforementioned group (c) can be contained in the decolorization agent in a total quantity of from about 0.1 to about 20.0% by weight, preferably from about 0.5 to about 10.0% by weight, and particularly preferably from about 1.0 to about 8.0% by weight—each based on the total weight of the decolorization agent.

Furthermore, the agents as contemplated herein preferably contain at least one surfactant from the group of anionic, cationic, amphoteric, and/or zwitterionic surfactants.

In a particularly preferential further embodiment, an agent as contemplated herein additionally contains at least one surfactant from the group of anionic, amphoteric, and/or zwitterionic, nonionic, and/or cationic surfactants.

Surfactants are amphiphilic (bifunctional) compounds, which includes at least one hydrophobic and at least one hydrophilic moiety. The hydrophobic residue is preferably a hydrocarbon chain comprising 8-24 carbon atoms, which can be saturated or unsaturated and linear or branched. Said $C_8$-$C_{24}$-alkyl chain is quite preferably linear.

In regard to anionic surfactants, the hydrophilic moiety comprises a negatively charged hydrophilic headgroup. The negatively charged hydrophilic headgroup can, for example, be a carboxylic acid group or the salt of a carboxylic acid group, a sulfonic acid group or the salt of the sulfonic acid group, a sulfuric acid ester group or the salt thereof, a phosphonic acid group or the salt of the phosphonic acid group, or a phosphoric acid ester group or the salt thereof.

The cosmetic agent as contemplated herein normally comprises an aqueous carrier. The aforementioned hydrophilic headgroups of the anionic surfactant—for example, carboxylic acid and the salts of carboxylic acids—are present in an aqueous solution in equilibrium, which state is also determined by the pH value of the agent. For example, if a fatty acid is thus used as an anionic surfactant, then a small portion of the fatty acid will remain in aqueous solution in the form of the protonated fatty acid, whereas the majority of the fatty acid will be deprotonated in aqueous solution and transformed in this manner into the salt of the fatty acid. For this reason, the definition of an anionic surfactant also includes a surfactant having an—as yet protonated—acid group.

An anionic surfactant (b) in terms of the present disclosure does not contain any cationic groupings, meaning that zwitterionic surfactants are not included within the definition of an anionic surfactant.

Therefore, inventive anionic surfactants have a water-solubilizing anionic group, for example a carboxylate, sulfate, sulfonate or phosphate group, and a lipophilic alkyl group comprising around 8 to 30 carbon atoms. In addition, glycol or polyglycol ether groups, ester and ether and amide groups, as well as hydroxyl groups may also be present in the molecule. Typical examples of anionic surfactants are alkylbenzene sulfonate, alkanesulfonate, olefin sulfonate, alkylether sulfonate, glyceryl ether sulfonate, α-methylestersulfonate, sulfofatty acids, alkyl sulfates, fatty alcohol ether sulfate, glyceryl ether sulfate, hydroxy mixed ether sulfate, monoglyceride-(ether) sulfate, fatty acid amide (ether)sulfate, mono- and dialkylsulfosuccinate, mono- and dialkylsulfosuccinamate, sulfotriglyceride, amide soaps, ether carboxylic acids and salts thereof, fatty acid isethionate, fatty acid sarcosinate, fatty acid tauride, acyl lactylate, acyltartrate, acylglutamate, acylaspartate, alkyloligoglucoside sulfate, protein-fatty acid condensates (in particular wheat-based plant products), and alkyl(ether)phosphate. If the anionic surfactants contain polyglycol ether chains, they may exhibit a conventional homolog distribution, preferably, however, a narrow homolog distribution.

Exemplary anionic surfactants as contemplated herein are respectively in the form of sodium-, potassium- and ammonium- as well as mono-, di- and trialkanol ammonium salts comprising from 2 to 4 carbon atoms in the alkanol group, linear and branched fatty acids comprising 8 to 30 carbon atoms (soaps), ether carboxylic acids of formula R—O—($CH_2$—$CH_2O$)$_x$—$CH_2$—COOH, in which r is a linear alkyl group comprising from 8 to 30 carbon atoms and x=0 or from 1 to 16, acyl sarcoside comprising from 8 to 24 carbon atoms in the acyl group, acyl tauride comprising from 8 to 24 carbon atoms in the acyl group, acyl isethionates comprising from 8 to 24 carbon atoms in the acyl group, which are available through esterification of fatty acids with the sodium salt of 2-hydroxyethane sulfonic acid (isethionic acid). In regard to this esterification, if fatty acids comprising 8 to 24 carbon atoms are used, thus for example lauric, myristic, palmitic, or stearic acid as well as technical fatty acid fractions, for example those $C_{12}$-$C_{18}$-fatty acid fractions obtainable from coconut fatty acid, then the suitable $C_{12}$-$C_{18}$-acyl isethionates preferable as contemplated herein will be obtained, sulfosuccinic acid mono- and dialkylesters comprising from 8 to 24 carbon atoms in the alkyl group and sulfosuccinic acid monoalkyl polyoxyethylesters comprising from 8 to 24 carbon atoms in the alkyl group and 1 to 6 oxyethyl groups, sulfosuccinic acid mono- and dialkyl esters can be produced by reacting maleic acid anhydride with a fatty alcohol comprising 8-24 carbon atoms to obtain the maleic acid monoester of the fatty alcohol, then further reacting it with sodium sulfite into a sulfosuccinic acid ester. Particularly suitable sulfosuccinic acid esters are derived from fat alcohol fractions comprising 12-18 carbon atoms, for example those from coconut fatty acid or coconut fatty acid methyl esters available through hydrogenation, linear alkane sulfonates comprising from 8 to 24 carbon atoms, linear alpha-olefin sulfonates comprising from 8 to 24 carbon atoms, alpha-sulfo fatty acid methyl esters of fatty acids comprising from 8 to 30 carbon atoms, alpha-sulfo fatty acid methyl esters of formula R—O($CH_2$—$CH_2O$)$_x$—$OSO_3H$, in which r is preferably a linear alkyl group comprising from 8 to 30 carbon atoms and x=0 or from 1 to 12, hydroxy sulfonates essentially according to at least one of the two following formulas or mixtures thereof as well as salts thereof $CH_3$—$(CH_2)_y$—CHOH—$(CH_2)_p$—(CH—$SO_3M$)-$(CH_2)_z$—$CH_2$—$CH_2$—O—$(C_nH_{2n}O)_x$—H, and/or $CH_3$—$(CH_2)_y$—(CH—$SO_3M$)-$(CH_2)_p$—CHOH—$(CH_2)_z$—$CH_2$—O—$(C_nH_{2n}O)_x$—H, wherein for both formulas y and z=0 or whole numbers from 1 to 18, p=0, 1, or 2 and the sum of (y+z+p) is a number from 12 to 18, x=0 or a number from 1 to 30, and n is a whole number from 2 to 4, and M is hydrogen or an alkali metal ion, in particular sodium, potassium, lithium, or an alkaline earth ion, in particular magnesium, calcium, zinc, and/or an ammonium ion, which can optionally be substituted, in particular mono-, di-, tri- or tetraammonium ions comprising C1 to C4 alkyl, alkenyl or aryl residues, sulfated hydroxyalkyl polyethylene- and/or hydroxyalkylene propyleneglycol ethers of formula $(CHOSO_3M)$-$CHR^3$—$(OCHR^4$—$CH_2)n$-$OR^2$, where $R^1$ is a linear alkyl residue comprising 1 to 24 carbon atoms, $R^2$ is a linear or branched, saturated alkyl residue comprising from 1 to 24 carbon atoms, $R^3$ is hydrogen or a linear alkyl residue comprising from 1 to 24 carbon atoms, $R^4$ is hydrogen or a methyl residue, and M is hydrogen, ammonium, alkylammonium, alkanolammonium, where the alkyl- and alkanol residues each comprise up to 4 carbon atoms or a metal atom selected from among lithium, sodium, potassium, calcium or magnesium, and n is a number in the range of from 0 to 12, and the total number of carbon atoms contained in $R^1$ and $R^3$ is from 2 to 44, sulfonates of unsaturated fatty acids comprising from 8 to 24 carbon atoms and from 1 to 6 double bonds, esters of tartaric acid and citric acid comprising alcohols that exhibit addition products of around 2-15 molecules of ethylene oxide and/or propylene oxide on fatty alcohols comprising from 8 to 22 carbon atoms, alkyl and/or alkenyl ether phosphate of formula, $R^1(OCHH_2CH_2)_n$—O—(PO—OX)—$OR^2$, in which $R^1$ is preferably an aliphatic hydrocarbon residue comprising from 8 to 30 carbon atoms, $R^2$ is hydrogen, a residue $(CH_2CH_2O)_nR^2$ or X, n equals numbers from 1 to 10, and X is hydrogen, an alkali or alkaline earth metal $NR^3R^4R^5R^6$, where $R^3$ to $R^6$, independently of each other, are hydrogen or a $C_1$-$C_4$-hydrocarbon residue, sulfated fatty acid alkylene glycol esters of formula $RCO(AlkO)_nSO_3M$ in which RCO— is a linear or branched, aliphatic, saturated and/or unsaturated acyl residue comprising from 6 to 22 carbon atoms, Alk is $CH_2CH_2$, $CHCH_3CH_2$ and/or $CH_2CHCH_3$ n equals numbers from about 0.5 to about 5, and M is a metal such as an alkali metal, in particular sodium, potassium, lithium, an alkaline earth metal, in particular magnesium, calcium, zinc, or an ammonium ion, such as $^+NR^3R^4R^5R^6$, where $R^3$ to $R^6$, independently of each other, are hydrogen or a $C_1$-$C_4$-hydrocarbon residue, monoglyceride sulfate and monoglyceride ether sulfate of formula $R^8OC$—$(OCH_2CH_2)_x$—$OCH_2$—[CHO$(CH_2CH_2O)_yH$]—$CH_2O(CH_2CH_2O)_z$—$SO_3X$, in which $R^8CO$ is a linear or branched acyl residue comprising from 6 to 22 carbon atoms, the sum of x, y and z equals 0 or numbers from 1 to 30, preferably from 2 to 10, and X is an alkali or alkaline earth metal. Typical examples of monoglyceride(ether)sulfates suitable in terms of the present disclosure are the reaction products of lauric acid monoglyceride, coconut fatty acid monoglyceride, palmitic acid monoglyceride, stearic acid monoglyceride, oleic acid monoglyceride, and tallow fatty acid monoglyceride as well as ethylene oxide adducts thereof with sulfur trioxide or chlorosulfonic acid in the form of their sodium salts. The use of monoglyceride sulfates in which $R^8CO$ represents a linear acyl residue comprising from 8 to 18 carbon atoms is preferred, amide ether carboxylic acids, $R^1$—CO—$NR^2$—$CH_2CH_2$—O—$(CH_2CH_2O)_n CH_2COOM$, where $R^1$ is a straight-chain or branched alkyl or alkyl residue comprising a number of carbon atoms in the chain of from 2 to 30, n is a whole number from 1 to 20, and $R^2$ is hydrogen, a methyl, ethyl, propyl, isopropyl, n-butyl, t-butyl, or iso-butyl residue, and M is hydrogen or a metal such as an alkali metal, in particular sodium, potassium, lithium, an alkaline earth metal, in particular magnesium, calcium, zinc, or an ammonium ion, such as $+NR^3R^4R^5R^6$, where $R^3$ bis $R^6$, independently of each other, are hydrogen or a C1 to C4-hydrocarbon residue. Products of this kind are available, for example, from the Chem-Y company under the product name Akypo®, and acylglutamates of formula XOOC—$CH_2CH_2CH(C(NH)OR$—COOX, in which RCO is a linear or branched acyl residue comprising from 6 to 22 carbon atoms and 0 and/or 1, 2, or 3 double bonds, and X is hydrogen, an alkaline and/or alkaline earth metal, ammonium, alkylammonium, alkanolammonium or glucammonium.

The agent as contemplated herein may also contain one or more amphoteric and/or zwitterionic surfactants. In the case of the zwitterionic surfactants, the hydrophilic moiety comprises a zwitterionic structural unit, hence a structural unit comprising both a cationically charged and an anionically charged moiety. Particularly suitable zwitterionic surfactants (b) as contemplated herein have an actinically charged moiety in the form of a quaternary ammonium group, and their anionic moiety is in the form of a —$SO_3^-$ or —$COO^-$ grouping.

An ammonium group is quaternary if a grouping of the type $(R_aR_bR_cR_dN)^+$ is present, meaning if all four hydrogen atoms of the NH4 ion from which the quaternary ammonium group is derived are replaced by organic residuals R (for example $R_a$ to $R_d$).

The —SO3 grouping of the zwitterionic surfactant present can be directly bonded to a carbon atom. In this case, the anionic part of the zwitterionic compound is a deprotonated sulfonic acid group.

Examples of particularly suitable zwitterionic surfactants are betaine, N-alkyl-N,N-dimethylammonium glycinate, N-acyl-aminopropyl-N,N-dimethylammonium glycinate, and 2-alkyl-3-carboxymethyl-3-hydroxyethyl imidazoline.

In embodiments, agents suitable in terms of the present disclosure contain at least one amphoteric surfactant. Preferred amphoteric surfactants are N-alkyl glycines, N-alkylpropionic acids, N-alkylaminobutyric acids, N-alkylaminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-coconutalklyl aminopropionate, as coconut acyl-aminoethylaminopropionate and $C_{12}$-$C_{18}$acylsarcosine.

Furthermore, it has proven to be advantageous if the agent contains additional non-ionogenic surface-active substances. Preferred nonionic surfactants are alkyl poly glycosides, as well as alkylene oxide adducts on fatty alcohols, fatty acids and fatty acid glycerides, each yielding from 2 to 50 moles of ethylene oxide per mole of fatty alcohol or fatty acid. Preparations having outstanding properties are also obtained if they contain fatty acids of ethoxylated glycerin as nonionic surfactants. It is most preferable if, as a nonionic surfactant, the agent contains an ethoxylated castor oil comprising in each case from 2 to 50 moles of ethylene oxide per mole of fatty acid, or an ethoxylated, hydrogenated castor oil comprising in each case from 2 to 50 moles of ethylene oxide per mole of fatty acid. The use of PEG-40 castor oil is particularly preferable in this context.

The agent as contemplated herein may also contain one or more cationic surfactants. Cationic surfactants are understood to be surfactants, thus surface-active compounds, each having one or more positive charges. Cationic surfactants contain only positive charges. These surfactants are normally composed of a hydrophobic part and a hydrophilic headgroup, the hydrophobic part usually including a hydrocarbon skeleton (thus including one or two linear or branched alkyl chains), and the positive charge(s) are located in the hydrophilic headgroup. Cationic surfactants adsorb at interfaces and aggregate in aqueous solution above the critical micelle concentration to positively charged micelles.

Exemplary cationic surfactants are quaternary ammonium compounds able to bear as hydrophobic residues one or two alkyl chains having a chain length of from 8 to 28 carbon atoms quaternary phosphonium salts substituted with one or more alkyl chains having a chain length of from 8 to 28 carbon atoms or tertiary sulfonium salts.

Furthermore, the cationic charge can also be in the form of an onium structural component in a heterocyclic ring (for example, an imidazolium ring or a pyridinium ring). In addition to the functional unit that carries the cationic charge, the cationic surfactant can also contain other uncharged functional groups, esterquats being one example of these. Preferred as contemplated herein is the use of cationic surfactants of the quaternary ammonium type, the esterquat type, and the amidoamine type. Preferred quaternary ammonium compounds are ammonium halogenides, in particular chlorides and bromides such as alkyltrimethylammonium chloride, dialkyldimethylammonium chloride and trialkylmethylammonium chloride, for example, cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27 and Quaternium-83. The long alkyl chains of the aforementioned surfactants preferably comprise from 10 to 18 carbon atoms. Esterquats are well-known substances that contain as a structural element both at least one ester function and at least one quaternary ammonium group. Preferred esterquats are quaternized ester salts of fatty acids with triethanolamine, quaternized ester salts of fatty acids with diethanolalkylamines and quaternized ester salts of fatty acids with 1,2-dihydroxypropyldialkylamines. The alkylamidoamines are usually produced by amidation of natural or synthetic fatty acids and fatty acids cuts with dialkylaminoamines. A compound from this substance group that is especially suitable as contemplated herein is the stearamidopropyldimethylamine available commercially under the name Tegoamid® S 18. Additional cationic surfactants suitable as contemplated herein include the quaternized protein hydrolysates.

The anionic, amphoteric, or zwitterionic, nonionic and cationic surfactants can be contained in a quantity of from about 0.1 to about 15.0% by weight, preferably of from about 0.25 to about 12.0% by weight, more preferably of from about 1.25 to about 10.0% by weight, and most preferably of from about 1.50 to about 9.0% by weight—each based on the total weight of the agent.

Furthermore, it has been found that the use of polyols further aids the decolorization effect. For this reason, it is preferable if the decolorization agents as contemplated herein additionally contain one or more polyols.

A polyol is understood to be a compound comprising at least two aliphatic (hence non-phenolic) OH groups. Exemplary polyols suitable as contemplated herein are, in particular, ethylene glycol, 1,2-propylene glycol, 1,3-propanediol, 1,2-butanediol, 1,3-butanediol, 1,2-pentanediol, 1,3-Pentanediol, 1-4-pentanediol, 1,5-pentanediol, 1,2-hexanediol, 1,3-hexanediol, 1,4-hexanediol, 1,5-hexanediol and 1,6-hexanediol. However, polyethylene glycol and polypropylene glycol are also suitable.

In a further embodiment, a decolorization agent as contemplated herein additionally contains one or more polyols from the group of ethylene glycol (1,2-ethanediol, 1,2-propanediol, 1,3-propanediol, 1,2-butanediol, 1,3-butanediol, 1,4-butanediol, 1,2-pentanetiol, 1,3-pentanetiol, 1-4-pentanetiol 1,5-pentanetiol, 1,2-hexanediol, 1,3-hexanediol, 1,4-hexanetiol, 1,5-hexanediol and 1,6-hexanediol.

The polyols are to be used in the decolorization agent as contemplated herein in a total quantity of from about 0.5 to about 15.0% by weight, preferably of from about 2.5 to about 13.5% by weight, more preferably of from about 3.5 to about 11.5% by weight, and particularly preferably from about 4.5 to about 9.5% by weight-based on the total weight of the agent.

Depending on the colorants previously used and depending on the condition, the degree of damage to, and the thickness of the hair, the duration of the decolorization process can vary from person to person. Although the decolorization process is generally intended to be completed within the normal application period of up to about 90 minutes, it will be significantly more convenient for the user of the decolorizing agent to be able to directly observe the decolorization process and rinse out the decolorizing agent immediately after the decolorization process is complete—possibly after only 20 or 30 minutes.

The direct observation of the decolorization process is possible for the user or hairdresser if the decolorization agent is fabricated in the form of a transparent gel.

Therefore, in a further preferential embodiment, a decolorization agent as contemplated herein is a clear, flowable gel formulation with a transmittance T of at least about 70%, preferably of at least about 75%, more preferably of at least about 80%, and most preferably of at least about 85%, wherein the transmittance T is calculated using the following formula $$T = \Phi_{ex}/\Phi_{in}$$

where $\Phi_{ex}$ equals the radiation intensity of the light beam emitted after having passed through the agent, and $\Phi_{in}$ equals the radiation intensity of the light beam entering the agent.

Gel systems are understood to be made from solid material of colloidal distribution including a thickening agent or a gelling agent as well as a liquid (water or water-solvent mixtures). The thickening or gelling agent in this case forms a spatial network within the liquid.

In terms of the present disclosure, the gels are flowable, meaning that they preferably exhibit a viscosity of from about 100 mPas to about 15,000 mPas, more preferably of from about 3,000 mPas to about 8,000 mPas (measured using a Brookfield rotary viscometer, spindle size 4, 25° C., and 20 rpm).

Transmittance describes the degree to which the test light (preferably daylight) permeates the gel and is expressed as the transmittance T.

Transmittance is expressed as a ratio T=Φex/Φin, whereby the radiation intensity of the light beam emitted after having passed through the agent Φex is put in relation to the radiation intensity of the light beam Φin entering the agent. The measurement is performed using daylight (daylight lamp) at a gel thickness of 1 cm (meaning that the gel to be measured is filled into a cuvette so that the gel present has a thickness of 1 cm before measurement using a commercially available photometer). At a transmittance of at least about 70%, preferably of at least about 75%, more preferably of at least about 80%, and most preferably of at least about 85%, the gel is so transparent that the consumer will be able to observe the hair decolorization process directly through the transparent gel after its application to the hair.

In this way, the consumer will be able to visually discern the completion of the decolorization process directly and without having to rinse the decolorizing agent away from a test strand of the treated hair.

Exemplary gelling agents or thickening agents for producing the transparent gel are anionic synthetic polymers, cationic synthetic polymers, nonionic guar gum, scleroglucan gum, xanthan gum, gum arabic, carrageenan gum, agar-agar, locust bean gum, pectins, alginates, starches, celluloses, and cellulosic derivatives, and/or synthetic polymers.

Therefore, in a further preferred embodiment, a decolorization agent as contemplated herein additionally contains at least one thickening agent selected from the group of anionic synthetic polymers, cationic synthetic polymers, nonionic guar gum, scleroglucan gum, xanthan gum, gum arabic, carrageenan gum, agar-agar, locust bean gum, pectins, alginates, starches, celluloses, and cellulosic derivatives, and/or synthetic polymers.

The agent as contemplated herein concerns a decolorization agent used for the decolorization of previously dyed keratin fibers, in particular human hair. The dyed keratin fibers are normally fibers that were previously dyed using conventional oxidation dyes and/or substantive dyes known to a person skilled in the art. The decolorization agents are suitable for the removal of colorations having been produced on the keratin fibers using oxidation dyes based on developer and coupler components. If the following compounds are used as developers, the colorations produced thereby can be thoroughly and effectively removed with nearly no subsequent darkening: p-phenylenediamine, p-toluenediamine-N,N-bis-(β-hydroxyethyl)-p-phenylenediamine, 4-N,N-bis-(β-hydroxyethyl)-amino-2-methylaniline, 2-(α,β-hydroxyethyl)-p-phenylendiamine, 2-(β-dihydroxyethyl)-p-phenylenediamine, 2-hydroxymethyl-p-phenylenediamine, bis-(2-hydroxy-5-aminophenyl)-methane, p-aminophenol, 4-amino-3-methylphenol, 2,4,5,6-tetraaminopyrimidine, 4-hydroxy-2,5,6-triaminopyrimidine, 2-hydroxy-4,5,6-triaminopyrimidine and/or 4,5-diamino-1-(β-hydroxyethyl)-pyrazole.

By using following compounds as couplers, the colorations thus produced are also able to be removed with very good decolorization results: m-phenylenediamine derivatives, naphthols, resorcinols and resorcinol derivatives, pyrazolones, and m-aminophenol derivatives. Suitable coupler substances are, in particular, 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-pyrazolone-5, 2,4-dichloro-3-aminophenol, 1,3-bis-(2',4'-diaminophenoxy)-propane, 2-chloro-resorcinol, 4-chloro-resorcinol, 2-chloro-6-methyl-3-aminophenol, 2-amino-3-hydroxypyridine, 2-methylresorcinol, 5-methylresorcinol, and 2-methyl-4-chloro-5-aminophenol, 1-naphthol, 1,5-dihydroxynaphthalene, 2,7-dihydroxynaphthalene, 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methyresorcinol, 2,5-dimethylresorcinol, and 2,6-dihydroxy-3,4-dimethylpyridine.

The decolorization agents as contemplated herein are intended for the removal of said colorations, and thus contain no dyes themselves, hence neither oxidation dye precursors of the developer type nor the coupler type, nor substantive dyes.

In a further preferential embodiment, an agent as contemplated herein is exemplified by the total quantity of the substantive dyes and oxidation dye precursors contained in the agent being a maximum amount of about 0.2% by weight, preferably a maximum of about 0.1% by weight, more preferably a maximum of about 0.05% by weight, and most preferably a maximum of about 0.01% by weight-based on the total weight of the agent. All of the embodiments and quantities described above are based upon the decolorizing agent that is ready to use, meaning the agent that is ready for application and can be applied by the user directly to the previously dyed keratin fibers. The decolorization effect of said ready-to-use decolorization agent is a function of its pH value, which is ideally in the acidic range. The pH values for the strongest observable decolorization are within the acid range of from about 0.5 to about 5.0, preferably of from about 0.6 to about 3.5, and particularly preferably of from about 0.8 to about 2.0. Therefore, the ready-to-use decolorization agent should be adjusted to pH values of from about 0.5 to about 5.0, preferably of from about 0.6 to about 3.5, and particularly preferably of from about 0.8 to about 2.0.

For the purpose of storage, however, the decolorization agent is preferably adjusted to an alkaline pH value, as the compounds in formulas (I) and (II) exhibit better stability at alkaline pH values. For these reasons, it is advantageous to adjust the alkaline storage pH of the decolorization agent to an acidic value shortly before application. Therefore, the pH of the formerly alkaline agent should be lowered shortly before application. Acidifying the formerly alkaline decolorization agent shortly before application can be accomplished by mixing two different agents, whereby the aforementioned first agent adjusted to an alkaline value is mixed with another agent containing one or more acids.

For practical purposes, the components necessary for producing the ready-to-use agent are provided to the user in the form of a kit (meaning in the form of a multi-component packaging unit) comprising at least two separately fabricated preparations (A) and (B).

The first preparation (A) in this context contains the reducing agent of formula (I) (and optionally the compounds of formula (II)), whereas the second component (B) comprises the acids necessary for lowering pH. The ready-to-use decolorization agent is then produced by mixing the preparations (A) and (B).

Therefore, a further object of the present disclosure is a multi-component packaging unit (kit of parts) for the reductive decolorization of dyed keratin fibers, comprising at least two separately fabricated preparations (A) and (B), wherein
the first preparation (A) contains, in a cosmetic carrier, at least one compound of formula (I) and, as disclosed in detail in the description of the first object of the present disclosure, optionally at least one compound of formula (II), and the second preparation (B)—based on the total weight of preparation (B)—has a water content of from about 5.0 to about 99.0% by weight, contains at least one inorganic and/or one organic acid, and has a pH value in the range of from about 0 to about 4.5, preferably of from about 0 to about 3.5.

Acids suitable for use are, for example, one or more acids from the group of citric acid, tartaric acid, malic acid, lactic acid, acetic acid, sulfuric acid, hydrochloric acid, phosphoric acid, methanesulfonic acid, benzoic acid, malonic acid, oxalic acid, pyruvic acid, oxaloacetic acid (oxobutanedioic acid), and/or 1-hydroxyethane-1,1-diphosphonic acid.

In a particularly preferred embodiment, a multi-component packaging unit (kit of parts) as contemplated herein contains at least one acid in the second preparation (B), wherein the at least one acid is selected from the group of citric acid, tartaric acid, malic acid, lactic acid, acetic acid, sulfuric acid, hydrochloric acid, phosphoric acid, methanesulfonic acid, benzoic acid, malonic acid, oxalic acid, pyruvic acid, oxaloacetic acid (oxobutanedioic acid), and/or 1-hydroxyethane-1,1-diphosphonic acid.

All pH values refer to pH values measured at a temperature of 20° C. The pH can be measured, for example, using a model N61 glass electrode from the Schott company.

In a preferential embodiment, the preparation (A) in the multi-component packaging unit is preferably an aqueous preparation with a water content of from about 5.0 to about 99.0% by weight, preferably of from about 15.0 to about 98.0% by weight, and particularly preferably from about 50-98% by weight.

The basis for calculating the water content here, which is specified as % by weight, is the mass of water contained in the total mass of the agent. The pH of the preparation (A) can have a value of from about 7.5 to about 12.0, preferably of from about 8.0 to about 11.5, more preferably of from about 8.5 to about 11.0, and particularly preferably of from about 9.0 to about 10.5.

In a particularly preferred embodiment, a multi-component packaging unit (kit of parts) as contemplated herein has—based on the total weight of preparation (A)—a water content in the first preparation (A) of from about 5.0 to about 99.0% by weight, preferably of from about 15.0 to about 98.0% by weight, particularly preferably from about 50 to about 98% by weight, and has a pH value of from about 7.5 to about 12.0, preferably of from about 8.0 to about 11.5, more preferably of from about 8.5 to about 11.0, and particularly preferably of from about 9.0 to about 10.5.

Alkalizing agents as contemplated herein usable for adjusting the pH of preparation (A) can be selected from the group consisting of ammonia, the alkanolamines, the basic amino acids as well as inorganic alkalizing agents such as alkaline earth and alkali metal hydroxides, alkaline earth and alkali metal silicates, alkaline earth and alkali metal phosphates, and alkaline earth and alkali metal hydrogen phosphates. Suitable inorganic alkalizing agents are sodium hydroxide, potassium hydroxide, sodium silicate, and sodium metasilicate. Organic alkalizing agents usable as contemplated herein can be selected from among monoethanolamine, 2-amino-2-methylpropanol, and triethanolamine. Basic amino acids usable as alkalizing agents as contemplated herein can be selected from the group consisting of arginine, lysine, ornithine, and histidine.

It is particularly preferable that the decolorization agent as contemplated herein be brought to an alkaline pH level by the use of one or more alkalizing agents from the group consisting of sodium hydroxide, potassium hydroxide, ammonia, monoethanolamine and/or arginine. It is most preferable that sodium hydroxide and/or potassium hydroxide be selected from this group.

In a further preferential embodiment, a decolorization agent as contemplated herein additionally contains one or more alkalizing agents selected from the group consisting of sodium hydroxide, potassium hydroxide, ammonia, monoethanolamine and/or arginine, particularly preferably selected from the group consisting of sodium hydroxide and/or potassium hydroxide.

As described earlier, the ready-to-use decolorization agent is preferably produced by the mixing of two preparations (A) and (B). In principle, the preparations (A) and (B) can be mixed in various ratios, for example that of (A)/(B) from about 20:1 to about 1:20. The preparations (A) and (B) are preferably mixed together at a ratio of from about 1:10 to about 10:1, particularly preferably of from about 1:2 to about 2:1. The mixing ratios in this regard are indicated by the ratio of the respective masses of preparations (A) and (B).

The preparations (A) and (B) are fabricated separately from one another, and each may be present as formulated in any container suitable for this purpose. Examples of suitable containers are glass—or in particular plastic—bottles, cans, tubes, or other suitable containers. To produce the ready-to-use mix, agent (A) can be transferred in its entirety from container (I) into container (II), which already contains agent (B).

In this case, the size of container (II) is chosen so that container (II) is able to accept the entire quantity of agents (A) and (B) and also allow for the mixing of both agents (A) and (B), for example by shaking or stirring.

Similarly, the mixture can be produced by transferring agent (B) in its entirety from container (II) into container (I)—which already contains agent (A).

In this case, the size of container (II) should be chosen so that container (II) is able to accept the entire quantity of agents (A) and (B) and also allow for the mixing of both agents (A) and (B), for example by shaking or stirring.

One additional way of producing the application mixture is to transfer both agents (A) and (B) in their entirety from both containers (I) and (II) into a third container, which then allows for the mixing of both agents—for example by shaking or stirring.

Example: A multi-component packaging unit as contemplated herein contains:

100 g of preparation (A) in container (I)
50 g of preparation (B) in container (II)

To prepare the application mixture, preparation (B) is transferred in its entirety from container (II) into container (I). Preparations (A) and (B) are then shaken or stirred together. The mixing ratio of preparations (A)/(B) is in the amount of (100 g/50 g)=2:1.

The multi-component packaging unit (kit of parts) can also comprise a third further separately fabricated preparation (C). This will particularly be the case if component (A), which contains the reducing agent of formula (I), is to be fabricated free of water.

In this case, the reducing agent of formula (I), which contains preparation (A), is initially mixed with the aqueous preparation (C): this mixing procedure ensures the complete dissolution of the compounds of formula (I) (and optionally the compounds of formula (II)). To produce the final application mixture, the mixture made from preparations (A) and (C) is then mixed with preparation (B), thereby setting a pH that is optimal for application.

In this case, a particularly preferential multi-component packaging unit (kit of parts) has a water content in the first preparation (A) of from about 0 to about 5.0% by weight, preferably of from about 0 to about 2.5% by weight, more preferably of from about 0 to about 1.0% by weight, and particularly preferably of from about 0 to about 0.1% by weight, and at least one further preparation (C) fabricated separately from preparations (A) and (B), wherein the third preparation (C)—based on the total weight of preparation (C)—has a water content of from about 5.0 to about 99.0% by weight, preferably of from about 15.0 to about 85.0% by weight.

Furthermore, the agents (A) and (B) as well as optionally (C) may contain additional ingredients, auxiliaries, and additives for improving decolorization performance and for adjusting additional desirable properties of the agent. For example, the agent can additional contain one or more of the following: nonionic polymers, for example, vinylpyrrolidinone/vinyl acrylate copolymers, polyvinylpyrrolidinone, vinylpyrrolidinone/vinyl acetate copolymers, polyethylene glycols, and polysiloxanes; additional silicones such as volatile or nonvolatile straight-chain, branched, or cyclic, crosslinked or uncrosslinked polyalylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy, and/or hydroxyl groups (dimethicone copolyols), linear polysiloxane(A)-polyoxyalkylene(B) block copolymers, grafted silicone polymers; cationic polymers such as quaternized cellulose ethers, polysiloxanes having quaternary groups, dimethyldiallylammonium chloride polymers, acrylamide/dimethyldiallylammonium chloride copolymers, dimethylaminoethyl methacrylate/vinylpyrrolidinone copolymers quaternized with diethyl sulfate, vinylpyrrolidinone/imidazolinium methochloride copolymers, and quaternized polyvinyl alcohol; zwitterionic and amphoteric polymers; anionic polymers such as, for example, polyacrylic acids or crosslinked polyacrylic acids; structuring agents such as glucose, maleic acid, and lactic acid, hair-conditioning compounds such as phospholipids, for example lecithin and kephalins; perfume oils, dimethylisosorbide, and cyclodextrins; fiber-structure-improving active substances, in particular mono-, di- and oligosaccharides, for example glucose, galactose, fructose, fruit sugars, and lactose; dyes for coloring the agent; anti-dandruff active substances such as piroctone olamine, zinc omadine and climbazol; amino acids and oligopeptides, in particular arginine and/or serine; animal- and/or plant-based protein hydrolysates, for example protein hydrolysates of elastin, collagen, keratin, silk, and milk, or protein hydrolysates of almond, rice, bean, potato, and wheat, as well as derivatives in the form of fatty acid condensation products thereof or optionally anionically or cationically modified derivatives; light-protection agents, such as derivatized benzophenones, cinnamic acid derivatives, and triazines; active substances such as panthenol, pantothenic acid, pantolactone, allantoin, pyrrolidinonecarboxylic acids and salts thereof, as well as bisabolol; polyphenols, in particular hydroxycinnamic acids, 6,7-dihydroxycumarins, hydroxybenzoic acids, catechins, tannins, leucoanthocyanidines, anthocyanidines, flavanones, flavones, and flavonols; ceramides or pseudoceramides; vitamins, provitamins, and vitamin precursors; plant extracts; swelling and penetration substances such as glycerol, propylene glycol monoethyl ether, carbonates, hydrogen carbonates, guanidines, ureas, as well as primary, secondary, and tertiary phosphates; luster agents such as ethylene glycol mono- and distearate as well as PEG-3 distearate; pigments, and propellants such as propane/butane mixtures, N2O, dimethyl ether, CO2, and air. Reference is made expressly to the relevant works known to one skilled in the art, for example Kh. Schrader, Grundlagen und Rezepturen der Kosmetika [Fundamentals and Formulations of Cosmetics], 2nd ed., Hiithig Buch Verlag, Heidelberg, 1989.

Further preferential embodiments regarding the multi-component packaging unit (kit of parts) as contemplated herein apply mutatis mutandis to the agents as contemplated herein.

The inventive agents and the multi-component packaging (kit-of-parts) described earlier herein can be used in a method for the coloration and the reductive decolorization of keratin fibers, especially human hair.

Therefore, a third object of the present disclosure is a method for the coloration and reductive decolorization of keratin fibers, in particular human hair, comprising the following steps and in the sequence specified (I) Application of a cosmetic dye containing at least one substantive dye and/or at least one oxidative dye precursor to the keratin fibers (II) Allowing the dye to act for a period of from about 5 to about 60 minutes before rinsing out the dye (III) Rinsing out the dye (IV) Application of a decolorization agent as disclosed in detail in the description of the first object of the present disclosure, (V) Allowing the decolorization agent to act at from about 20 to about 45° C. for a period of from about 5 to about 60, preferably of from about 10 to about 55 minutes, more preferably of from about 15 to about 55 minutes, and particularly preferably of from about 20 to about 50 minutes, (VI) Rinsing out the decolorization agent, (VII) Optionally, application of an after-treatment agent to the keratin fibers, whereby the after-treatment agent contains at least one surfactant from the group consisting of anionic, cationic, nonionic amphoteric, and/or zwitterionic surfactants.

Steps (I), (II), and (III) of the method constitute the keratin fiber dyeing process and are consequently performed in immediate, successive chronological order. In principle, there is no time limit for the sequence of steps (III) and (IV). Step (IV) can thus take place hours, days, or even, for example, up to six weeks after the completion of step (III).

However, the method is intended to remove the undesirable result from the dyeing process in steps (I) to (III), so it is self-evident that the decolorization is only able to be performed if the dyed fibers still also demonstrate the undesirable coloration result. For example, if the keratin fibers had been dyed using substantive dyes and this coloration had already completely washed out after 2 weeks, then a decolorization procedure taking place thereafter would be neither necessary nor as contemplated herein.

In step (IV) of the method as contemplated herein, a ready-to-use decolorization agent from the first object of the present disclosure is applied to the keratin fibers.

Said ready-to-use decolorization agent can be a single-component agent that is applied to the keratin fibers directly from the container in which it was fabricated. As previously described, stability considerations make it preferable for the ready-to-use decolorization agent to be prepared shortly before application by mixing together (at least) two preparations (A) and (B) fabricated separately from one another. As was disclosed in detail in the description of the second object of the present disclosure, the preparation of the ready-to-use decolorization agent can, for example, take place by mixing together the preparations in the multi-component packaging unit (kit of parts).

Steps (IV), (V), and (VI) of the method constitute the keratin fiber decolorization process and are consequently again performed in immediate, successive chronological order.

Step (VII) of the method, meaning the application of an after-treatment agent, is optional. Nor is there a time limit for the sequence of step (VI) and the optional step (VII).

However, it is advantageous if the after-treatment in step (VII) takes places a maximum of two days after the completion of step (VI). The after-treatment, step (VII), can also be repeated more than once, for example if the after-treatment agent is a shampoo.

Particularly preferable is a method for the coloration and reductive decolorization of keratin fibers, in particular human hair, comprising the following steps and in the sequence specified (I) Application of a cosmetic dye containing at least one substantive dye and/or at least one oxidative dye precursor to the keratin fibers (II) Allowing the dye to act for a period of from about 5 to about 60 minutes before rinsing out the dye (III) Rinsing out the dye (IV) Application of a decolorization agent as disclosed in detail in the description of the first object of the present disclosure, (V) Allowing the decolorization agent to act at from about 20 to about 45° C. for a period of from about 5 to about 120 minutes, preferably of from about 10 to about 100 minutes, more preferably of from about 15 to about 90 minutes, and particularly preferably of from about 20 to about 60 minutes, (VI) Rinsing out the decolorization agent, (VII) Optionally, application of an after-treatment agent to the keratin fibers, whereby the after-treatment agent contains at least one surfactant from the group consisting of anionic, cationic, amphoteric, and/or zwitterionic surfactants.

Further preferential embodiments regarding the method as contemplated herein apply mutatis mutandis to said agents as contemplated herein as well as to said multi-component packaging unit (kit of parts) as contemplated herein.

EXAMPLES

Coloration
The following formulations were produced (specified as % by weight):

| Color creme (F1) | |
|---|---|
| Raw material | % by weight |
| Cetearyl alcohol | 6.6 |
| C12-C18 fatty alcohols | 2.4 |
| Ceteareth-20 | 0.6 |
| Ceteareth-12 | 0.6 |
| Plantacare 1200 UP (lauryl glucoside 50-53% aqueous solution) | 2.0 |
| Sodium laureth-6 carboxylate (21% aqueous solution) | 10.0 |
| Sodium myreth sulphate (68-73% aqueous solution) | 2.8 |
| Sodium acrylate, trimethylammoniopropylacrylamide chloride copolymer | 3.8 |
| Sodium hydroxide | 0.26 |
| p-toluenediamine, Sulfate | 0.48 |
| m-aminophenol | 0.02 |
| 4-chlororesorcinol | 0.09 |
| 2-methylresorcinol | 0.04 |
| Resorcinol | 0.12 |
| Ammonium sulfate | 0.71 |

| Color creme (F1) | |
|---|---|
| Raw material | % by weight |
| Sodium sulfite | 0.4 |
| Ascorbic acid | 0.1 |
| 1-hydroxyethane-1,1-diphosphonic acid (60% aqueous solution) | 0.2 |
| Sodium silicate (waterglass) | 0.5 |
| L-serine | 1.0 |
| Ammonia (25% aqueous solution) | 6.7 |
| Water | up to 100 |

| Color creme (F2) | |
|---|---|
| Raw material | % by weight |
| Cetearyl alcohol | 8.5 |
| C12-C18 fatty alcohols | 2.4 |
| Ceteareth-20 | 0.6 |
| Ceteareth-12 | 0.6 |
| Plantacare 1200 UP (lauryl glucoside, 50-53% aqueous solution) | 2.0 |
| Sodium laureth-6 carboxylate (21% aqueous solution) | 10.0 |
| Sodium myreth sulphate (68-73% aqueous solution) | 2.8 |
| Sodium acrylate, trimethylammoniopropylacrylamide chloride copolymer (19-21% aqueous solution) | 3.8 |
| Potassium hydroxide | 0.83 |
| p-toluenediamine, Sulfate | 0.89 |
| m-aminophenol | 0.04 |
| 2-methylresorcinol | 0.10 |
| Resorcinol | 0.17 |
| 4-chlororesorcinol | 0.08 |
| 2-amino-3-hydroxypyridine | 0.03 |
| 2.7-dihydroxynaphthalene | 0.09 |
| Glycine | 1.0 |
| Sodium sulfite | 0.4 |
| Ascorbic acid | 0.1 |
| 1-hydroxyethane-1,1-diphosphonic acid (60% aqueous solution) | 0.2 |
| Sodium silicate (waterglass) | 0.5 |
| Marula oil | 0.6 |
| Monoethanolamine | 5.0 |
| Water | up to 100 |

| Oxidizing agents (Ox) | |
|---|---|
| Raw material | % by weight |
| Sodium benzoate | 0.04 |
| Dipicolinic acid | 0.1 |
| Disodium pyrophosphate | 0.1 |
| Potassium hydroxide | 0.09 |
| 1,2-propylene glycol | 1.0 |
| 1-hydroxyethane-1,1-diphosphonic acid (60% aqueous solution) | 0.25 |
| Paraffinum liquidum | 0.30 |
| Steartrimonium chloride | 0.39 |
| Cetearyl alcohol | 3.4 |
| Ceteareth-20 | 1.0 |
| Hydrogen peroxide (50% aqueous solution) | 12.0 |

The hair strands (Kerling Euro-Natur hair, white) were measured colorimetrically and the respective L-value determined (as a measure of the brightness of the hair strand).

The color cremes (F1 and F2) and the oxidizing agent (Ox) were then mixed together at a proportion of 1:1 and applied to strands of hair (Kerling Euro-Natur hair, white).

The weight ratio of application mixture to hair was 4:1, and the time of action was 30 minutes at a temperature of 32 degrees Celsius. The hair strands were subsequently rinsed with water, dried, and left to rest at room temperature for at least 24 hours.

Thereafter, the hair strands (Kerling Euro-Natur hair, white) were again measured colorimetrically and the new L-value determined (as a measure of the brightness of the hair strand).

The strands were dyed a shade of dark blonde (F1+OX) or a shade of mocha brown (F2+Ox).

1.2. Decolorization

The following formulations were produced (all entries in % by weight active substance):

| Preparation (A) | |
|---|---|
| Raw material | % by weight |
| Xanthan gum | 0.8 |
| Propylene glycol | 1.6 |
| Cocamidopropyl betaine (40% aqueous solution) | 4.0 |
| Cyclanon Eco (aqueous solution of the compounds $N(CH_2SO_2Na)_3$ and $N(CH_2SO_3Na)_3$ at a molar ratio of 1:1) | 20.0 |
| Water | up to 100 |
| pH value | 9.0-10.5 |

| Preparation (B) | |
|---|---|
| Raw material | % by weight |
| Xanthan gum | 0.9 |
| Propylene glycol | 1.8 |
| Cocamidopropyl betaine (40% aqueous solution) | 4.4 |
| Sulfuric acid (20% aqueous solution) | 12.0 |
| Water | up to 100 |
| pH value | 0.5 |

Preparations (A) and (B) were mixed together at a ratio of 1:1 and applied to the previously dyed hair strands.

The weight ratio of application mixture to hair was 4:1, and the time of action was 30 minutes at a temperature of 32 degrees Celsius. The hair strands were subsequently rinsed with water, dried, and left to rest at room temperature for at least 24 hours.

Thereafter, the hair strands (Kerling Euro-Natur hair, white) were again measured colorimetrically and the new L-value determined (as a measure of the brightness of the hair strand).

The evaluation of the decolorization result was made based on the determined ΔL value $$\Delta L = L(\text{after decolorization}) - L(\text{before decolorization})$$

The higher the ΔL value, the better the decolorization of the dyed hair strands.

| F1 + OX | L value | ΔL value |
|---|---|---|
| dyed hair | 33.1 | 23.8 |
| decolorized hair | 56.9 | |

| F2 + OX | L value | ΔL value |
|---|---|---|
| dyed hair | 25.7 | 25.5 |
| decolorized hair | 51.2 | |

After the application of the decolorization agent as contemplated herein (a mixture of preparations (A) and (B)), both the strands dyed with F1+OX and the strands dyed with F2+OX were decolorized to a significant extent.

Further exemplary formulations

| Preparation (C) | |
|---|---|
| Raw material | % by weight |
| Xanthan gum | 0.8 |
| Propylene glycol | 1.6 |
| Cocamidopropyl betaine (40% aqueous solution) | 4.0 |
| Cyclanon Eco (aqueous solution of the compounds $N(CH_2SO_2Na)_3$ and $N(CH_2SO_3Na)_3$ at a molar ratio of 1:1) | 20.0 |
| Water | up to 100 |
| pH value | 9.0-10.5 |

| Preparation (D) | |
|---|---|
| Raw material | % by weight |
| Cetearyl alcohol | 2.66 |
| PEG-40 castor oil | 0.50 |
| Sodium cetearyl sulfate | 0.17 |
| Hydroxyethane-1,1-disposphonic acid (1-etidronic acid) | up to pH 0.5 |
| Water (dist.) | up to 100 |

Preparations (C) and (D) were mixed together at a ratio of 1:1 and applied to the hair strands dyed previously with dye (F1+OX). The weight ratio of application mixture (decolorization agent) to hair was 4:1, and the time of action was 30 minutes at a temperature of 32 degrees Celsius.

The hair strands were subsequently rinsed with water, dried, and left to rest at room temperature for at least 24 hours. The hair was decolorized to a significant extent.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Multi-component packaging unit (kit of parts) for the reductive decolorization of dyed keratin fibers, comprising at least two separately fabricated preparations (A) and (B), wherein the first preparation (A) comprises, in a cosmetic carrier, at least one compound of formula (I)

$$A[(CR^1R^2)SO_2M]_{p,q} \qquad (I)$$

in which

A represents $N(R^3)_{3-q}$ or $O(R^4)_{2-p}$, $R^1$, $R^2$, $R^4$ independently of one another represent a hydrogen atom or a $C_1$-$C_6$-alkyl group, $R^3$ represents identical or different residues selected from the group of a hydrogen atom, a $C_1$-$C_{20}$-alkyl group, and a $C_3$-$C_8$-cycloalkyl group optionally substituted with one to three $C_1$-$C_4$-alkyl residues, M represents identical or different residues selected from a hydrogen atom or an equivalent of an alkali metal ion, alkaline earth metal ion, or metal ion, p represents the numbers 1 or 2,
q represents the numbers 1, 2, or 3,
wherein
at least one of the residues $R^1$, $R^2$, $R^4$ represents a $C_1$-$C_6$-alkyl group if A represents $O(R^4_{2-p})$, and $R^3$ does not represent a hydrogen atom if q equals 1,
and
optionally, at least one compound of formula (II)

wherein A, $R^1$, $R^2$, $R^3$, $R^4$, M, p and q have the same general meaning as in formula (I), wherein the selection of these variables does not have to be the same for the compounds of formulas (I) and (II) in the specific individual case, and the second preparation (B)—based on the total weight of preparation (B)—has a water content of from about 5.0 to about 99.0% by weight, comprises at least one inorganic and/or one organic acid, and has a pH value in the range of from about 0 to about 4.5.

2. Multi-component packaging unit (kit of parts) according to claim 1, wherein the second preparation (B) comprises at least one acid selected from the group of citric acid, tartaric acid, malic acid, lactic acid, acetic acid, sulfuric acid, hydrochloric acid, phosphoric acid, methanesulfonic acid, benzoic acid, malonic acid, oxalic acid, pyruvic acid, oxaloacetic acid (oxobutanedioic acid), and/or 1-hydroxyethane-1,1-diphosphonic acid.

3. Multi-component packaging unit (kit-of-parts) according to claim 1, wherein the first preparation (A)—based on the total weight of preparation (A)—has a water content of from about 5.0 to about 99.0% by weight, and has a pH value of from about 7.5 to about 12.0.

4. Multi-component packaging unit (kit-of-parts) according to claim 1, wherein
the first preparation (A)—based on the total weight of preparation (A)—has a water content of from about 0 to about 5.0% by weight, and the multi-component packaging unit comprises at least one further preparation (C) fabricated separately from preparations (A) and (B), wherein
the third preparation (C)—based on the total weight of preparation (C)—has a water content of from about 5.0 to about 99.0% by weight.

5. Method for the coloration and reductive decolorization of keratin fibers, in particular human hair, comprising the following steps and in the sequence specified
(I) Applying a cosmetic dye comprising at least one substantive dye and/or at least one oxidative dye precursor to the keratin fibers,
(II) Allowing the dye to act for a period of from about 5 to about 60 minutes,
(III) Rinsing out the dye,
(IV) Applying a decolorization agent to the keratin fibers, wherein the agent comprises, in a cosmetic carrier
(a) at least one compound of formula (I) $A[(CR^1R^2)SO_2M]_{p,q}$ (I)
in which
A represents $N(R^3)_{3-q}$ or $O(R^4)_{2-p}$,
$R^1$, $R^2$, $R^4$ independently of one another represent a hydrogen atom or a $C_1$-$C_6$-alkyl group,
$R^3$ represents identical or different residues selected from the group of a hydrogen atom, a $C_1$-$C_{20}$-alkyl group, and a $C_3$-$C_8$-cycloalkyl group optionally substituted with one to three $C_1$-$C_4$-alkyl residues, M represents identical or different residues selected from a hydrogen atom or an equivalent of an alkali metal ion, alkaline earth metal ion, or metal ion,
p represents the numbers 1 or 2,
q represents the numbers 1, 2, or 3,
wherein
at least one of the residues $R^1$, $R^2$, $R^4$ represents a $C_1$-$C_6$-alkyl group if A represents $O(R^4_{2-p})$, and $R^3$ does not represent a hydrogen atom if q equals 1,
and
(b) optionally, at least one compound of formula (II)

wherein A, $R^1$, $R^2$, $R^3$, $R^4$, M, p and q have the same general meaning as in formula (I), wherein the selection of these variables does not have to be the same for the compounds of formulas (I) and (II) in the specific individual case,
(V) Allowing the decolorization agent to act at from about 20 to about 45° C. for a period of from about 5 to about 60 minutes,
(VI) Rinsing out the decolorization agent, and
(VII) Optionally, applying an after-treatment agent to the keratin fibers, wherein the after-treatment agent comprises at least one surfactant chosen from the group of anionic, cationic, nonionic amphoteric, and/or zwitterionic surfactants.

6. Multi-component packaging unit (kit-of-parts) according to claim 3, wherein the first preparation (A)—based on the total weight of preparation (A)—has a water content of from about 50-98% by weight, and has a pH value of from about 9.0 to about 10.5.

7. Multi-component packaging unit (kit-of-parts) according to claim 1, wherein
the first preparation (A) has a water content of from about 0 to about 0.1% by weight, and the multi-component packaging unit comprises at least one further preparation (C) fabricated separately from preparations (A) and (B), wherein
the third preparation (C)—based on the total weight of preparation (C)—has a water content of from about 15.0 to about 85.0% by weight.

8. Multi-component packaging unit (kit-of-parts) according to claim 1, wherein the first preparation (A)—based on the total weight of preparation (A)—has a water content of from about 15.0 to about 98.0% by weight and a pH value of from about 8.0 to about 11.5.

9. Multi-component packaging unit (kit-of-parts) according to claim 1, wherein the first preparation (A)—based on the total weight of preparation (A)—has a water content of from about 50 to about 98.0% by weight and a pH value of from about 8.5 to about 11.

10. Multi-component packaging unit (kit-of-parts) according to claim 1, wherein each of $R^1$ and $R^2$ is a hydrogen atom.

11. Multi-component packaging unit (kit-of-parts) according to claim 1, wherein q is 3.

12. Multi-component packaging unit (kit-of-parts) according to claim 1, wherein the at least one compound of formula (I) is selected from the group of
$HN(CH_2SO_2Na)_2$, disodium[(sulfinatomethyl)amino]methanesulfinate,
$HN(CH_2SO_2K)_2$, disodium[(sulfinatomethyl)amino]methanesulfinate,
$HN(CH_2SO_2H)_2$, [(sulfinomethyl)amino]methanesulfinic acid, $N(CH_2SO_2Na)_3$, tri sodium[bis(sulfinatomethyl)amino]methanesulfinate,
$N(CH_2SO_2K)_3$, tripotassium[bis(sulfinatomethyl)amino]methanesulfinate,
$N(CH_2SO_2H)_3$, [bis(sulfinomethyl)amino]methanesulfinic acid,
$H_2NCH(CH_3)SO_2Na$, sodium 1-aminoethane-1-sulfinate,
$H_2NCH(CH_3)SO_2K$, potassium 1-aminoethane-1-sulfinate,
$H_2NCH(CH_3)SO_2H$, 1-aminoethane-1-sulfinic acid,
$HN(CH(CH_3)SO_2Na)_2$, disodium 1-[(1-sulfinatoethyl)amino]ethane-1-sulfinate,
$HN(CH(CH_3)SO_2K)_2$, dipotassium 1-[(1-sulfinatoethyl)amino]ethane-1-sulfinate,
$HN(CH(CH_3)SO_2H)_2$, 1-[(1-sulfinoethyl)amino]ethane-1-sulfinic acid,
$N(CH(CH_3)SO_2Na)_3$, trisodium 1-[bis(1-sulfinatoethyl)amino]ethane-1-sulfinate,
$N(CH(CH_3)SO_2K)_3$, tripotassium 1-[bis(1-sulfinatoethyl)amino]ethane-1-sulinate, and/or
$N(CH(CH_3)SO_2H)_3$, 1-[bis(1-sulfinoethyl)amino]ethane-1-sulfinic acid.

13. Multi-component packaging unit (kit-of-parts) according to claim 1, wherein at least one compound of formula (II) is present and is selected from the group of
$HN(CH_2SO_3Na)_2$, disodium[(sulfonatomethyl)amino]methanesulfonate,
$HN(CH_2SO_3K)_2$, dipotassium[(sulfonatomethyl)amino]methanesulfonate,
$HN(CH_2SO_3H)_2$, [(sulfomethyl)amino]methanesulfonic acid,
$N(CH_2SO_3Na)_3$, trisodium [bis(sulfonatomethyl)amino]methanesulfonate,
$N(CH_2SO_3K)_3$, tripotassium [bis(sulfonatomethyl)amino]methanesulfonate,
$N(CH_2SO_3H)_3$, [bis(sulfomethyl)amino]methanesulfonic acid,
$H_2NCH(CH_3)SO_3Na$, sodium 1-aminoethane-1-sulfonate,
$H_2NCH(CH_3)SO_3K$, potassium 1-aminoethane-1-sulfonate,
$H_2NCH(CH_3)SO_3H$, 1-aminoethane-1-sulfonic acid,
$HN(CH(CH_3)SO_3Na)_2$, disodium 1-[(1-sulfonatoethyl)amino]ethane-1-sulfonate,
$HN(CH(CH_3)SO_3K)_2$, dipotassium 1-[(1-sulfonatoethyl)amino]ethane-1-sulfonate,
$HN(CH(CH_3)SO_3H)_2$, 1-[(1-fulfoethyl)amino]ethane-1-sulfonic acid,
$N(CH(CH_3)SO_3Na)_3$, trisodium 1-[bis(1-sulfonatoethyl)amino]ethane-1-sulfonate,
$N(CH(CH_3)SO_3K)_3$, tripotassium 1-[bis(1-sulfonatoethyl)amino]ethane-1-sulfonate,
$N(CH(CH_3)SO_3H)_3$, 1-[bis(1-sulfoethyl)amino]ethane-1-sulfonic acid.

14. Multi-component packaging unit (kit-of-parts) according to claim 1, wherein—based on the total weight of preparation (A)—the preparation (A) comprises one or more compounds of formula (I) in a total quantity of from about 0.2 to about 20.0% by weight.

15. Multi-component packaging unit (kit-of-parts) according to claim 1, wherein—based on the total weight of preparation (A)—the preparation (A) comprises one or more compounds of formula (I) in a total quantity of from about 0.5 to about 6.0% by weight.

16. Method for the coloration and reductive decolorization of keratin fibers, according to claim 5, wherein the agent—based on the total weight of the agent—has a water content of from about 15.0 to about 98.0% by weight and a pH value of from about 8.0 to about 11.5.

17. Method for the coloration and reductive decolorization of keratin fibers, according to claim 5, wherein each of $R^1$ and $R^2$ is a hydrogen atom.

18. Method for the coloration and reductive decolorization of keratin fibers, according to claim 5, wherein q is 3.

19. Method for the coloration and reductive decolorization of keratin fibers, according to claim 5, wherein the at least one compound of formula (I) is selected from the group of
$HN(CH_2SO_2Na)_2$, disodium[(sulfinatomethyl)amino]methanesulfinate,
$HN(CH_2SO_2K)_2$, disodium[(sulfinatomethyl)amino]methanesulfinate,
$HN(CH_2SO_2H)_2$, [(sulfinomethyl)amino]methanesulfinic acid,
$N(CH_2SO_2Na)_3$, tri sodium[bis(sulfinatomethyl)amino]methanesulfinate,
$N(CH_2SO_2K)_3$, tripotassium[bis(sulfinatomethyl)amino]methanesulfinate,
$N(CH_2SO_2H)_3$, [bis(sulfinomethyl)amino]methanesulfinic acid,
$H_2NCH(CH_3)SO_2Na$, sodium 1-aminoethane-1-sulfinate,
$H_2NCH(CH_3)SO_2K$, potassium 1-aminoethane-1-sulfinate,
$H_2NCH(CH_3)SO_2H$, 1-aminoethane-1-sulfinic acid,
$HN(CH(CH_3)SO_2Na)_2$, disodium 1-[(1-sulfinatoethyl)amino]ethane-1-sulfinate,
$HN(CH(CH_3)SO_2K)_2$, dipotassium 1-[(1-sulfinatoethyl)amino]ethane-1-sulfinate,
$HN(CH(CH_3)SO_2H)_2$, 1-[(1-sulfinoethyl)amino]ethane-1-sulfinic acid,
$N(CH(CH_3)SO_2Na)_3$, trisodium 1-[bis(1-sulfinatoethyl)amino]ethane-1-sulfinate,
$N(CH(CH_3)SO_2K)_3$, tripotassium 1-[bis(1-sulfinatoethyl)amino]ethane-1-sulinate, and/or
$N(CH(CH_3)SO_2H)_3$, 1-[bis(1-sulfinoethyl)amino]ethane-1-sulfinic acid.

20. Method for the coloration and reductive decolorization of keratin fibers, according to claim 5, wherein (b) is present and comprises at least one compound of formula (II), which is selected from the group of
$HN(CH_2SO_3Na)_2$, disodium[(sulfonatomethyl)amino]methanesulfonate,
$HN(CH_2SO_3K)_2$, dipotassium[(sulfonatomethyl)amino]methanesulfonate,
$HN(CH_2SO_3H)_2$, [(sulfomethyl)amino]methanesulfonic acid,
$N(CH_2SO_3Na)_3$, trisodium [bis(sulfonatomethyl)amino]methanesulfonate,
$N(CH_2SO_3K)_3$, tripotassium [bis(sulfonatomethyl)amino]methanesulfonate,
$N(CH_2SO_3H)_3$, [bis(sulfomethyl)amino]methanesulfonic acid,
$H_2NCH(CH_3)SO_3Na$, sodium 1-aminoethane-1-sulfonate,
$H_2NCH(CH_3)SO_3K$, potassium 1-aminoethane-1-sulfonate,
$H_2NCH(CH_3)SO_3H$, 1-aminoethane-1-sulfonic acid,
$HN(CH(CH_3)SO_3Na)_2$, disodium 1-[(1-sulfonatoethyl)amino]ethane-1-sulfonate,
$HN(CH(CH_3)SO_3K)_2$, dipotassium 1-[(1-sulfonatoethyl)amino]ethane-1-sulfonate,
$HN(CH(CH_3)SO_3H)_2$, 1-[(1-fulfoethyl)amino]ethane-1-sulfonic acid, $N(CH(CH_3)SO_3Na)_3$, trisodium 1-[bis(1-sulfonatoethyl)amino]ethane-1-sulfonate,
$N(CH(CH_3)SO_3K)_3$, tripotassium 1-[bis(1-sulfonatoethyl)amino]ethane-1-sulfonate,
$N(CH(CH_3)SO_3H)_3$, 1-[bis(1-sulfoethyl)amino]ethane-1-sulfonic acid.

\* \* \* \* \*